United States Patent [19]
Yao et al.

[11] Patent Number: 5,869,286
[45] Date of Patent: Feb. 9, 1999

[54] RECEPTOR THAT BINDS IL-17

[75] Inventors: Zhengbin Yao, Lafayette, Colo.; Melanie K. Spriggs, Seattle; William C. Fanslow, Federal Way, both of Wash.

[73] Assignee: Immunex Corporation, Seattle, Wash.

[21] Appl. No.: 620,694

[22] Filed: Mar. 21, 1996

Related U.S. Application Data

[63] Continuation-in-part of Ser. No. 538,765, Aug. 7, 1995, abandoned, which is a continuation-in-part of Ser. No. 410,535, Mar. 23, 1995, abandoned.

[51] Int. Cl.⁶ ...................................................... C12N 1/00
[52] U.S. Cl. ........................ 435/69.1; 435/69.52; 435/7.1; 435/7.2; 435/252.3; 435/320.1; 536/23.5
[58] Field of Search ................................. 435/69.1, 320.1, 435/252.3; 536/23.5

[56] References Cited

FOREIGN PATENT DOCUMENTS

WO 95/18826  7/1995  WIPO .

OTHER PUBLICATIONS

*Immunity* 3(6) 1995, Yao et al pp. 811–821 (See Sequence Alignment).
*Genome Res.* 3(6) 1995, Trofalten et al, pp. 214–224.
Bowie et al, *Science* 247, 1990, pp. 1306–1310.
Ngo et al "The Protein Building Problem," Ed Merz et al, 1994, pp. 433,492–494.
Frommel et al. J. Evol Biol. 1989.
Nicholas et al., *Virol.* 179:1 89; 1990.
Rouvier et al., *J. Immunol.* 150:5445; 1993.
Albrecht et al., *J. Virol.* 66:5047;1992.
Torrance et al., "Inhibition of cytokine activity in collagen induced arthritis"m Poster presentation at University of Washington, Department of Immunology/Immunex Corporation Symposium.

*Primary Examiner*—Garnette D. Draper
*Attorney, Agent, or Firm*—Patricia Anne Perkins

[57] ABSTRACT

Isolated receptors for IL-17, DNA's encoding such receptors, and pharmaceutical compositions made therefrom, are disclosed. The isolated receptors can be used to regulate an immune response.

12 Claims, No Drawings

RECEPTOR THAT BINDS IL-17

CROSS-REFERENCE TO RELATED APPLICATION

This application is a continuation-in-part of U.S. application Ser. No. 08/538,765, filed Aug. 7, 1995, now abandoned, which is a continuation-in-part of U.S. application Ser. No. 08/410,535, filed Mar. 23, 1995, now abandoned.

TECHNICAL FIELD OF THE INVENTION

The present invention relates generally to the field of cytokine receptors, and more specifically to cytokine receptor proteins having immunoregulatory activity.

BACKGROUND OF THE INVENTION

Cytokines are hormone-like molecules that regulate various aspects of an immune or inflammatory response. Cytokines exert their effects by specifically binding receptors present on cells, and transducing a signal to the cells. Rouvier et al. (J. Immunol. 150:5445; 1993) reported a novel cDNA which they termed CTLA-8. The putative CTLA8 protein is 57% homologous to the predicted amino acid sequence of an open reading frame (ORF) present in Herpesvirus saimiri (HSV) referred to as HVS13 (Nicholas et al. Virol. 179:1 89, 1990; Albrecht et al., J. Virol. 66:5047;1992). However, the function, if any of either CTLA-8 or HVS13 was not known, nor was a receptor or binding protein for CTLA-8 or HVS13 known. Thus, prior to the present invention, there was a need in the art to determine the function of CTLA-8 and HVS13, and to identify receptor molecules or binding proteins that play a role in the function of these proteins.

SUMMARY OF THE INVENTION

The present invention identifies a novel receptor that binds IL-17 (CTLA-8) and HVS13, a viral homolog of IL-17; DNAs encoding the novel receptor and novel receptor proteins are provided. The receptor is a Type I transmembrane protein; the mouse receptor has 864 amino acid residues, the human receptor has 866 amino acid residues. Soluble forms of the receptor can be prepared and used to regulate immune responses in a therapeutic setting; accordingly, pharmaceutical compositions comprising soluble forms of the novel receptor are also provided. Deleted forms and fusion proteins comprising the novel receptor, and homologs thereof are also disclosed. Also provided are methods of regulating an immune response, and methods of suppressing rejection of grafted organs or tissue. These and other aspects of the present invention will become evident upon reference to the following detailed description of the invention.

DETAILED DESCRIPTION OF THE INVENTION

A soluble IL-17 (CTLA-8) protein and an ORF present in Herpesvirus saimiri (HVS13) were expressed as fusion proteins comprising an immunoglobulin Fc region, and used to screen cells for expression of a receptor for IL-17. T cell thymoma EL4 cells were found to bind the HVS13/Fc as well as murine CTLA8 (IL-17)/Fc fusion protein. A cDNA library from EL4 cells was prepared and screened for expression of the receptor. The receptor is a Type I transmembrane protein with 864 amino acid residues, which is referred to as IL-17R (CTLA-8R). Various forms of IL-17R were prepared, including IL-17R/Fc protein, a soluble IL-17R which contains the signal peptide and extracellular domain of IL-17R, and a soluble IL-17R/Flag® construct. A human IL-17R was isolated from a human peripheral blood lymphocyte library by cross-species hybridization, and exhibits similarities to the murine IL-17R.

IL-17, HVS13 and homologous proteins

CTLA-8 refers to a cDNA cloned from an activated T cell hybridoma clone (Rouvier et al., J. Immunol. 150:5445; 1993). Northern blot analysis indicated that CTLA-8 transcription was very tissue specific. The CTLA-8 gene was found to map at chromosomal site 1a in mice, and at 2q31 in humans. Although a protein encoded by the CTLA-8 gene was never identified by Rouvier et al, the predicted amino acid sequence of CTLA-8 was found to be 57% homologous to the predicted amino acid sequence of an ORF present in Herpesvirus Saimiri, HVS13. The CTLA-8 protein is referred to herein as Interleukin-17 (IL-17).

The complete nucleotide sequence of the genome of HVS has been reported (Albrecht et al., J. Virol. 66:5047; 1992). Additional studies on one of the HVS open reading frames (ORFs), HVS13, are described in Nicholas et al., Virol. 179:1 89; 1990. HVS13 is a late gene which is present in the Hind III-G fragment of HVS. Antisera developed against peptides derived from HVS13 are believed to react with a late protein (Nicholas et al., supra).

As described U.S. Ser. No. 08/462,353, now abandoned, a CIP of U.S. Ser. No. 08/410,536, filed Mar. 23, 1995, now abandoned, full length murine CTLA-8 protein and a CTLA-8/Fc fusion protein were expressed, tested, and found to act as a costimulus for the proliferation of T cells. Human IL-17 (CTLA-8) was identified by probing a human T cell library using a DNA fragment derived from degenerate PCR; homologs of IL-17 (CTLA-8) are expected to exist in other species as well. A full length HVS13 protein, as well as an HVS13/Fc fusion protein, were also expressed, and found to act in a similar manner to IL-17 (CTLA-8) protein. Moreover, other species of herpesviruses are also likely to encode proteins homologous to that encoded by HVS13.

Proteins and Analogs

The present invention provides isolated IL-17R and homologs thereof having immunoregulatory activity. Such proteins are substantially free of contaminating endogenous materials and, optionally, without associated native-pattern glycosylation. Derivatives of IL-17R within the scope of the invention also include various structural forms of the primary protein which retain biological activity. Due to the presence of ionizable amino and carboxyl groups, for example, an IL-17R protein may be in the form of acidic or basic salts, or may be in neutral form. Individual amino acid residues may also be modified by oxidation or reduction.

The primary amino acid structure may be modified by forming covalent or aggregative conjugates with other chemical moieties, such as glycosyl groups, lipids, phosphate, acetyl groups and the like, or by creating amino acid sequence mutants. Covalent derivatives are prepared by linking particular functional groups to amino acid side chains or at the N- or C-termini.

Soluble forms of IL-17R are also within the scope of the invention. The nucleotide and predicted amino acid sequence of the murine IL-17R is shown in SEQ ID NOs:1 and 2. Computer analysis indicated that the protein has an N-terminal signal peptide with a cleavage site between amino acid 31 and 32. Those skilled in the art will recognize that the actual cleavage site may be different than that predicted by computer analysis. Thus, the N-terminal amino acid of the cleaved peptide is expected to be within about five amino acids on either side of the predicted cleavage site. The signal peptide is followed by a 291 amino acid extracellular domain, a 21 amino acid transmembrane domain, and a 521 amino acid cytoplasmic tail. Soluble IL-17R comprises the signal peptide and the extracellular domain (residues 1 to 322 of SEQ ID NO:1) or a fragment thereof. Alternatively, a different signal peptide can be substituted for residues 1 through 31 of SEQ ID NO:1.

The nucleotide and predicted amino acid sequence of the human IL-17R is shown in SEQ ID NOs:9 and 10. It shares many features with the murine IL-17 R. Computer analysis indicated that the protein has an N-terminal signal peptide with a cleavage site between amino acid 27 and 28. Those skilled in the art will recognize that the actual cleavage site may be different than that predicted by computer analysis. Thus, the N-terminal amino acid of the cleaved peptide is expected to be within about five amino acids on either side of the predicted cleavage site. The signal peptide is followed by a 293 amino acid extracellular domain, a 21 amino acid transmembrane domain, and a 525 amino acid cytoplasmic tail. Soluble IL-17R comprises the signal peptide and the extracellular domain (residues 1 to 320 of SEQ ID NO:1) or a fragment thereof. Alternatively, a different signal peptide can be substituted for the native signal peptide.

Other derivatives of the IL-17R protein and homologs thereof within the scope of this invention include covalent or aggregative conjugates of the protein or its fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its site of synthesis to its site of function inside or outside of the cell membrane or wall (e.g., the yeast α-factor leader).

Protein fusions can comprise peptides added to facilitate purification or identification of IL-17R proteins and homologs (e.g., poly-His). The amino acid sequence of the inventive proteins can also be linked to an identification peptide such as that described by Hopp et al., *Bio/Technology* 6:1204 (1988). Such a highly antigenic peptide provides an epitope reversibly bound by a specific monoclonal antibody, enabling rapid assay and facile purification of expressed recombinant protein. The sequence of Hopp et al. is also specifically cleaved by bovine mucosal enterokinase, allowing removal of the peptide from the purified protein. Fusion proteins capped with such peptides may also be resistant to intracellular degradation in *E. coli.*

Fusion proteins further comprise the amino acid sequence of a IL-17R linked to an immunoglobulin Fc region. An exemplary Fc region is a human IgG1 having a nucleotide and amino acid sequence set forth in SEQ ID NO:4. Fragments of an Fc region may also be used, as can Fc muteins such as those described in U.S. Ser. No. 08/145,830, filed Oct. 29, 1993. Depending on the portion of the Fc region used, a fusion protein may be expressed as a dimer, through formation of interchain disulfide bonds. If the fusion proteins are made with both heavy and light chains of an antibody, it is possible to form a protein oligomer with as many as four IL-17R regions.

In another embodiment, IL-17R and homologs thereof further comprise an oligomerizing zipper domain. Zipper domains are described in U.S. Ser. No. 08/107,353, filed Aug. 13, 1993, the relevant disclosure of which is incorporated by reference herein. Examples of leucine zipper domains are those found in the yeast transcription factor GCN4 and a heat-stable DNA-binding protein found in rat liver (C/EBP; Landschulz et al., *Science* 243:1681, 1989), the nuclear transforming proteins, fos and jun, which preferentially form a heterodimer (O'Shea et al., *Science* 245:646, 1989; Turner and Tjian, *Science* 243:1689, 1989), and the gene product of the murine proto-oncogene, c-myc (Landschulz et al., *Science* 240:1759, 1988). The fusogenic proteins of several different including paramyxovirus, coronavirus, measles virus and many retroviruses, also possess leucine zipper domains (Buckland and Wild, *Nature* 338:547, 1989; Britton, *Nature* 353:394, 1991; Delwart and Mosialos, *AIDS Research and Human Retroviruses* 6:703, 1990).

Derivatives of IL-17R may also be used as immunogens, reagents in in vitro assays, or as binding agents for affinity purification procedures. Such derivatives may also be obtained by cross-linking agents, such as M-maleimidobenzoyl succinimide ester and N-hydroxysuccinimide, at cysteine and lysine residues. The inventive proteins may also be covalently bound through reactive side groups to various insoluble substrates, such as cyanogen bromide-activated, bisoxirane-activated, carbonyldiimidazole-activated or tosyl-activated agarose structures, or by adsorbing to polyolefin surfaces (with or without glutaraldehyde cross-linking). Once bound to a substrate, proteins may be used to selectively bind (for purposes of assay or purification) antibodies raised against the IL-17R or against other proteins which are similar to the IL-17R, as well as other proteins that bind IL-17R or its homologous proteins.

The present invention also includes IL-17R with or without associated native-pattern glycosylation. Proteins expressed in yeast or mammalian expression systems, e.g., COS-7 cells, may be similar or slightly different in molecular weight and glycosylation pattern than the native molecules, depending upon the expression system. Expression of DNAs encoding the inventive proteins in bacteria such as *E. coli* provides non-glycosylated molecules. Functional mutant analogs of IL-17R protein or homologs thereof having inactivated N-glycosylation sites can be produced by oligonucleotide synthesis and ligation or by site-specific mutagenesis techniques. These analog proteins can be produced in a homogeneous, reduced-carbohydrate form in good yield using yeast expression systems. N-glycosylation sites in eukaryotic proteins are characterized by the amino acid triplet Asn-$A_1$-Z, where $A_1$ is any amino acid except Pro, and Z is Ser or Thr. In this sequence, asparagine provides a side chain amino group for covalent attachment of carbohydrate. Such a site can be eliminated by substituting another amino acid for Asn or for residue Z, deleting Asn or Z, or inserting a non-Z amino acid between $A_1$ and Z, or an amino acid other than Asn between Asn and $A1_1$.

IL-17R protein derivatives may also be obtained by mutations of the native IL-17R or its subunits. A IL-17R mutated protein, as referred to herein, is a polypeptide homologous to a IL-17R protein but which has an amino acid sequence different from the native IL-17R because of one or a plurality of deletions, insertions or substitutions. The effect of any mutation made in a DNA encoding a IL-17R peptide may be easily determined by analyzing the ability of the mutated IL-17R peptide to inhibit costimulation of T or B cells by IL-17 (CTLA-8) or homologous proteins, or to bind proteins that specifically bind IL-17R (for example, antibodies or proteins encoded by the CTLA-8 cDNA or the HVS13 ORF). Moreover, activity of IL-17R analogs, muteins or derivatives can be determined by any of the assays methods described herein. Similar mutations may be made in homologs of IL-17R, and tested in a similar manner.

Bioequivalent analogs of the inventive proteins may be constructed by, for example, making various substitutions of residues or sequences or deleting terminal or internal residues or sequences not needed for biological activity. For example, cysteine residues can be deleted or replaced with other amino acids to prevent formation of incorrect intramolecular disulfide bridges upon renaturation. Other approaches to mutagenesis involve modification of adjacent dibasic amino acid residues to enhance expression in yeast systems in which KEX2 protease activity is present.

Generally, substitutions should be made conservatively; i.e., the most preferred substitute amino acids are those which do not affect the ability of the inventive proteins to bind their ligands in a manner substantially equivalent to that of native mIL-17R or hIL-17R. Examples of conservative substitutions include substitution of amino acids outside of the binding domain(s), and substitution of amino acids that do not alter the secondary and/or tertiary structure of IL-17R and homologs thereof. Additional examples include substituting one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known.

Similarly, when a deletion or insertion strategy is adopted, the potential effect of the deletion or insertion on biological activity should be considered. Subunits of the inventive proteins may be constructed by deleting terminal or internal residues or sequences. Fragments of IL-17R that bind IL-17 can be readily prepared (for example, by using restriction enzymes to delete portions of the DNA) and tested for their ability to bind IL-17. Additional guidance as to the types of mutations that can be made is provided by a comparison of the sequence of IL-17R to proteins that have similar structures, as well as by performing structural analysis of the inventive proteins.

Mutations in nucleotide sequences constructed for expression of analog IL-17R CTLA-8R) must, of course, preserve the reading frame phase of the coding sequences and preferably will not create complementary regions that could hybridize to produce secondary mRNA structures such as loops or hairpins which would adversely affect translation of the receptor mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutated viral proteins screened for the desired activity.

Not all mutations in the nucleotide sequence which encodes a IL-17R protein or homolog thereof will be expressed in the final product, for example, nucleotide substitutions may be made to enhance expression, primarily to avoid secondary structure loops in the transcribed MRNA (see EPA 75,444A, incorporated herein by reference), or to provide codons that are more readily translated by the selected host, e.g., the well-known *E. coli* preference codons for *E. coli* expression.

Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniques*, Jan. 1985, 12–19); Smith et al. (*Genetic Engineering: Principles and Methods*, Plenum Press, 1981); and U.S. Pat. Nos. 4,518,584 and 4,737,462 disclose suitable techniques, and are incorporated by reference herein.

Due to code degeneracy, there can be considerable variation in nucleotide sequences encoding the same amino acid sequence. Other embodiments include sequences capable of hybridizing under moderately stringent conditions (prewashing solution of 5×SSC, 0.5% SDS, 1.0 mM EDTA (pH 8.0) and hybridization conditions of 50° C., 5×SSC, overnight) to the DNA sequences encoding IL-17R, and other sequences which are degenerate to those which encode the IL-17R. In a preferred embodiment, IL-17R analogs are at least about 70% identical in amino acid sequence to the amino acid sequence of IL-17R proteins as set forth in SEQ ID NO:1 or SEQ ID NO:9. Similarly, analogs of IL-17R homologs are at least about 70% identical in amino acid sequence to the amino acid sequence of the native, homologous proteins. In a most preferred embodiment, analogs of IL-17R or homologs thereof are at least about 80% identical in amino acid sequence to the native form of the inventive proteins.

Percent identity may be determined using a computer program, for example, the GAP computer program described by Devereux et al. (*NucL. Acids Res.* 12:387, 1984) and available from the University of Wisconsin Genetics Computer Group (UWGCG). For fragments derived from the IL-17R protein, the identity is calculated based on that portion of the IL-17R protein that is present in the fragment. Similar methods can be used to analyze homologs of IL-17R.

The ability of IL-17R analogs to bind CTLA-8 can be determined by testing the ability of the analogs to inhibit IL-17 (CTLA-8)-induced T cell proliferation. Alternatively, suitable assays, for example, an enzyme immunoassay or a dot blot, employing CTLA-8 or HSV13 (or a homolog thereof which binds native IL-17R) can be used to assess the ability of IL-17R analogs to bind CTLA-8. Such methods are well known in the art.

The IL-17R proteins and analogs described herein will have numerous uses, including the preparation of pharmaceutical compositions. The inventive proteins will also be useful in preparing kits that are used to detect IL-17 or IL-17R, for example, in patient specimens. Such kits will also find uses in detecting the interaction of IL-17 and IL-17R, as is necessary when screening for antagonists or mimetics of this interaction (for example, peptides or small molecules that inhibit or mimic, respectively, the interaction). A variety of assay formats are useful in such kits, including (but not limited to) ELISA, dot blot, solid phase binding assays (such as those using a biosensor), rapid format assays and bioassays.

Expression of Recombinant Receptors for IL-17

The proteins of the present invention are preferably produced by recombinant DNA methods by inserting a DNA sequence encoding IL-17R protein or a homolog thereof into a recombinant expression vector and expressing the DNA sequence in a recombinant microbial expression system under conditions promoting expression. DNA sequences encoding the proteins provided by this invention can be assembled from cDNA fragments and short oligonucleotide linkers, or from a series of oligonucleotides, to provide a synthetic gene which is capable of being inserted in a recombinant expression vector and expressed in a recombinant transcriptional unit.

Recombinant expression vectors include synthetic or cDNA-derived DNA fragments encoding IL-17R, homologs, or bioequivalent analogs, operably linked to suitable transcriptional or translational regulatory elements derived from mammalian, microbial, viral or insect genes. Such regulatory elements include a transcriptional promoter, an optional operator sequence to control transcription, a sequence encoding suitable mRNA ribosomal binding sites, and sequences which control the termination of transcription and translation, as described in detail below. The ability to replicate in a host, usually conferred by an origin of replication, and a selection gene to facilitate recognition of transformants may additionally be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means contiguous and, in the case of secretory leaders, contiguous and in reading frame. DNA sequences encoding IL-17R or homologs which are to be expressed in a microorganism will preferably contain no introns that could prematurely terminate transcription of DNA into mRNA.

Useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed. *E. coli* is typically transformed using derivatives of pBR322, a plasmid derived from an *E. coli* species (Bolivar et al., *Gene* 2:95, 1977). pBR322 contains genes for ampicillin and tetracycline resistance and thus provides simple means for identifying transformed cells.

Promoters commonly used in recombinant microbial expression vectors include the β-lactamase (penicillinase) and lactose promoter system (Chang et al., *Nature* 275:615, 1978; and Goeddel et al., *Nature* 281:544, 1979), the tryptophan (trp) promoter system (Goeddel et al., *Nucl. Acids Res.* 8:4057, 1980; and EPA 36,776) and tac promoter (Maniatis, *Molecular Cloning: A Laboratory Manual*, Cold Spring Harbor Laboratory, p. 412, 1982). A particularly useful bacterial expression system employs the phage $\lambda P_L$ promoter and cI857ts thermolabile repressor. Plasmid vectors available from the American Type Culture Collection which incorporate derivatives of the $\lambda P_L$ promoter include plasmid pHUB2, resident in *E. coli* strain JMB9 (ATCC 37092) and pPLc28, resident in *E. coli* RR1 (ATCC 53082).

Suitable promoter sequences in yeast vectors include the promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPA 73,657.

Preferred yeast vectors can be assembled using DNA sequences from pBR322 for selection and replication in *E. coli* (Amp$^r$ gene and origin of replication) and yeast DNA sequences including a glucose-repressible ADH2 promoter and α-factor secretion leader. The ADH2 promoter has been described by Russell et al. (*J. Biol. Chem.* 258:2674, 1982) and Beier et al. (*Nature* 300:724, 1982). The yeast α-factor leader, which directs secretion of heterologous proteins, can be inserted between the promoter and the structural gene to be expressed. See, e.g., Kurjan et al., *Cell* 30:933, 1982; and Bitter et al., *Proc. Natl. Acad. Sci. USA* 81:5330, 1984. The leader sequence may be modified to contain, near its 3' end, one or more useful restriction sites to facilitate fusion of the leader sequence to foreign genes.

The transcriptional and translational control sequences in expression vectors to be used in transforming vertebrate cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the BglI site located in the viral origin of replication is included. Further, viral genomic promoter, control and/or signal sequences may be utilized, provided such control sequences are compatible with the host cell chosen. Exemplary vectors can be constructed as disclosed by Okayama and Berg (*Mol. Cell. Biol.* 3:280, 1983).

A useful system for stable high level expression of mammalian receptor cDNAs in C127 murine mammary epithelial cells can be constructed substantially as described by Cosman et al. (*Mol. Immunol.* 23:935, 1986). A preferred eukaryotic vector for expression of IL-17R DNA is referred to as pDC406 (McMahan et al., EMBO J. 10:2821, 1991), and includes regulatory sequences derived from SV40, human immunodeficiency virus (HIV), and Epstein-Barr virus (EBV). Other preferred vectors include pDC409 and pDC410, which are derived from pDC406. pDC410 was derived from pDC406 by substituting the EBV origin of replication with sequences encoding the SV40 large T antigen. pDC409 differs from pDC406 in that a Bgl II restriction site outside of the multiple cloning site has been deleted, making the Bgl II site within the multiple cloning site unique.

A useful cell line that allows for episomal replication of expression vectors, such as pDC406 and pDC409, which contain the EBV origin of replication, is CV-1/EBNA (ATCC CRL 10478). The CV-1/EBNA cell line was derived by transfection of the CV-1 cell line with a gene encoding Epstein-Barr virus nuclear antigen-1 (EBNA-1) and constitutively express EBNA-1 driven from human CMV immediate-early enhancer/promoter.

Host Cells

Transformed host cells are cells which have been transformed or transfected with expression vectors constructed using recombinant DNA techniques and which contain sequences encoding the proteins of the present invention. Transformed host cells may express the desired protein (IL-17R or homologs thereof), but host cells transformed for purposes of cloning or amplifying the inventive DNA do not need to express the protein. Expressed proteins will preferably be secreted into the culture supernatant, depending on the DNA selected, but may be deposited in the cell membrane.

Suitable host cells for expression of viral proteins include prokaryotes, yeast or higher eukaryotic cells under the control of appropriate promoters. Prokaryotes include gram negative or gram positive organisms, for example *E. coli* or Bacillus spp. Higher eukaryotic cells include established cell lines of mammalian origin as described below. Cell-free translation systems could also be employed to produce viral proteins using RNAs derived from the DNA constructs disclosed herein. Appropriate cloning and expression vectors for use with bacterial, fungal, yeast, and mammalian cellular hosts are described by Pouwels et al. (*Cloning Vectors: A Laboratory Manual*, Elsevier, N.Y., 1985), the relevant disclosure of which is hereby incorporated by reference.

Prokaryotic expression hosts may be used for expression of IL-17R or homologs that do not require extensive proteolytic and disulfide processing. Prokaryotic expression vectors generally comprise one or more phenotypic selectable markers, for example a gene encoding proteins conferring antibiotic resistance or supplying an autotrophic requirement, and an origin of replication recognized by the host to ensure amplification within the host. Suitable prokaryotic hosts for transformation include *E. coli, Bacillus subtilis, Salmonella typhimurium*, and various species within the genera Pseudomonas, Streptomyces, and Staphylococcus, although others may also be employed as a matter of choice.

Recombinant IL-17R may also be expressed in yeast hosts, preferably from the Saccharomyces species, such as *S. cerevisiae*. Yeast of other genera, such as Pichia or Kluyveromyces may also be employed. Yeast vectors will generally contain an origin of replication from the 2μ yeast plasmid or an autonomously replicating sequence (ARS), promoter, DNA encoding the viral protein, sequences for polyadenylation and transcription termination and a selection gene. Preferably, yeast vectors will include an origin of replication and selectable marker permitting transformation of both yeast and *E. coli*, e.g., the ampicillin resistance gene of *E. coli* and *S. cerevisiae* trp1 gene, which provides a selection marker for a mutant strain of yeast lacking the ability to grow in tryptophan, and a promoter derived from a highly expressed yeast gene to induce transcription of a structural sequence downstream. The presence of the trp1 lesion in the yeast host cell genome then provides an effective environment for detecting transformation by growth in the absence of tryptophan.

Suitable yeast transformation protocols are known to those of skill in the art; an exemplary technique is described by Hinnen et al., *Proc. Natl. Acad. Sci. USA* 75:1929, 1978, selecting for Trp$^+$ transformants in a selective medium consisting of 0.67% yeast nitrogen base, 0.5% casamino acids, 2% glucose, 10 μg/ml adenine and 20 μg/ml uracil. Host strains transformed by vectors comprising the ADH2 promoter may be grown for expression in a rich medium consisting of 1% yeast extract, 2% peptone, and 1% glucose supplemented with 80 μg/ml adenine and 80 μg/ml uracil. Derepression of the ADH2 promoter occurs upon exhaustion of medium glucose. Crude yeast supernatants are harvested by filtration and held at 4° C. prior to further purification.

Various mammalian or insect cell culture systems can be employed to express recombinant protein. Baculovirus systems for production of heterologous proteins in insect cells are reviewed by Luckow and Summers, *Bio/Technology* 6:47 (1988). Examples of suitable mammalian host cell lines include the COS-7 lines of monkey kidney cells, described by Gluzman (*Cell* 23:175, 1981), and other cell lines capable of expressing an appropriate vector including, for example, CV-1/EBNA (ATCC CRL 10478), L cells, C127, 3T3, Chinese hamster ovary (CHO), HeLa and BHK cell lines. Mammalian expression vectors may comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences.

Purification of Receptors for IL-17

Purified IL-17R, homologs, or analogs are prepared by culturing suitable host/vector systems to express the recombinant translation products of the DNAs of the present invention, which are then purified from culture media or cell extracts. For example, supernatants from systems which secrete recombinant protein into culture media can be first concentrated using a commercially available protein concentration filter, for example, an Amicon or Millipore Pellicon ultrafiltration unit.

Following the concentration step, the concentrate can be applied to a suitable purification matrix. For example, a suitable affinity matrix can comprise a counter structure protein or lectin or antibody molecule bound to a suitable support. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Gel filtration chromatography also provides a means of purifying the inventive proteins.

Affinity chromatography is a particularly preferred method of purifying IL-17R and homologs thereof. For example, a IL-17R expressed as a fusion protein comprising an immunoglobulin Fc region can be purified using Protein A or Protein G affinity chromatography. Moreover, a IL-17R protein comprising an oligomerizing zipper domain may be purified on a resin comprising an antibody specific to the oligomerizing zipper domain. Monoclonal antibodies against the IL-17R protein may also be useful in affinity chromatography purification, by utilizing methods that are well-known in the art. A ligand (i.e., IL-17 or HVS-13) may also be used to prepare an affinity matrix for affinity purification of IL-17R.

Finally, one or more reversed-phase high performance liquid chromatography (RP-HPLC) steps employing hydrophobic RP-HPLC media, e.g., silica gel having pendant methyl or other aliphatic groups, can be employed to further purify a IL-17R composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. Finally, high performance liquid chromatography (HPLC) can be employed for final purification steps. Microbial cells employed in expression of recombinant viral protein can be disrupted by any convenient method, including freeze-thaw cycling, sonication, mechanical disruption, or use of cell lysing agents.

Fermentation of yeast which express the inventive protein as a secreted protein greatly simplifies purification. Secreted recombinant protein resulting from a large-scale fermentation can be purified by methods analogous to those disclosed by Urdal et al. (*J. Chromatog.* 296:171, 1984). This reference describes two sequential, reversed-phase HPLC steps for purification of recombinant human GM-CSF on a preparative HPLC column.

Protein synthesized in recombinant culture is characterized by the presence of cell components, including proteins, in amounts and of a character which depend upon the purification steps taken to recover the inventive protein from the culture. These components ordinarily will be of yeast, prokaryotic or non-human higher eukaryotic origin and preferably are present in innocuous contaminant quantities, on the order of less than about 1 percent by weight. Further, recombinant cell culture enables the production of the inventive proteins free of other proteins which may be normally associated with the proteins as they are found in nature in the species of origin.

Administration of IL-17R Compositions

The present invention provides methods of using therapeutic compositions comprising an effective amount of a protein and a suitable diluent and carrier, and methods for regulating an immune response. The use of IL-17R or homologs in conjunction with soluble cytokine receptors or cytokines, or other immunoregulatory molecules is also contemplated. Moreover, DNA encoding soluble IL-17R will also be useful; a tissue or organ to be transplanted can be transfected with the DNA by any method known in the art. The organ or tissue thus expresses soluble IL-17R, which acts in the localized area of the graft to suppress rejection of the graft. Similar methods comprising administering such DNA's to the site of the graft will also show efficacy in ameliorating graft rejection.

For therapeutic use, purified protein is administered to a patient, preferably a human, for treatment in a manner appropriate to the indication. Thus, for example, IL-17R protein compositions administered to regulate immune function can be given by bolus injection, continuous infusion, sustained release from implants, or other suitable technique. Typically, a therapeutic agent will be administered in the form of a composition comprising purified IL-17R, in conjunction with physiologically acceptable carriers, excipients or diluents. Such carriers will be nontoxic to recipients at the dosages and concentrations employed.

Ordinarily, the preparation of such protein compositions entails combining the inventive protein with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with conspecific serum albumin are exemplary appropriate diluents. Preferably, product is formulated as a lyophilizate using appropriate excipient solutions (e.g., sucrose) as diluents. Appropriate dosages can be determined in trials. The amount and frequency of administration will depend, of course, on such factors as the nature and severity of the indication being treated, the desired response, the condition of the patient, and so forth.

Receptors for IL-17 (CTLA-8) can be administered for the purpose of inhibiting T cell proliferation, or for inhibiting T cell activation. Soluble IL-17R are thus likely to be useful in preventing or treating organ or graft rejection, autoimmune disease, allergy or asthma. The inventive receptor proteins will also be useful for prevention or treatment of inflammatory disease in which activated T cells play a role. Similarly, HVS13 and homologs thereof stimulate B cell proliferation and immunoglobulin secretion; thus, receptors that bind HVS13 or CTLA-8 will be useful in vivo to inhibit B cell proliferation or immunoglobulin secretion. Receptors for CTLA-8 will also be useful to inhibit the binding of HVS13 or CTLA-8 to cells expressing IL-17R.

The following examples are offered by way of illustration, and not by way of limitation. Those skilled in the art will recognize that variations of the invention embodied in the examples can be made, especially in light of the teachings of the various references cited herein, the disclosures of which are incorporated by reference.

EXAMPLE 1

This example describes identification of cells that express a receptor (or counterstructure) for HVS13/mCTLA8. A chimeric protein (HVS13 type II Fc) consisting of an Fc region of a human immunoglobulin (SEQ ID NO:4) followed by the amino acid 19 to 151 of HVS13 (SEQ ID NO:8) was prepared. A murine CTLA8/Fc (mCTLA8/Fc) was constructed by fusing amino acid 22 to 150 of mCTLA8 (SEQ ID NO:6) to the Fc region of human IgG1. A control Fc protein was constructed by a similar method. The HVS13/Fc and mCTLA-8 proteins were expressed and used to identify cell sources by flow cytometry.

Cells ($1 \times 10^6$) were preincubated on ice for 30 minutes in 100 µl of FACS buffer (PBS, 1% FCS and 0.1% NaN3) containing 2% normal goat serum and 2% normal rabbit serum to block nonspecific binding. 100 µl of HVS13/Fc, mCTLA-8/Fc or control/Fc protein was added at 5 µg/ml and incubated on ice for 30 min. After washing, the cells were stained with biotin labeled anti human IgG (Fc specific) followed by PE-conjugated streptavidin (Becton Dickson & Co, Mountain View, Calif.) in 100 µl of FACS buffer. Cells were then washed and analyzed using a FACScan (Becton Dickinson). A minimum of 5,000 cells were analyzed for each sample. More than a dozen cell lines were screened and it was found that both HVS13/Fc and mCTLA8/Fc fusion proteins bound specifically to the murine thymoma cell line EL4. These cells did not bind to the control/Fc fusion protein.

EXAMPLE 2

This example describes cloning of the gene that encodes IL-17R. After identification of a source for HVS13 counterstructure, an EL4 mammalian expression library was screened by a slide-binding autoradiographic method (Gearing et al., *EMBO J.* 8:3667, 1989). CV1/EBNA cells were maintained in Dulbecco's modified Eagle's medium (DMEM) containing 10% (v/v) fetal calf serum (FCS) at 37° C. in a humidified atmosphere containing 10% CO2 and passaged twice weekly. Subconfluent CV1/EBNA cell monolayers on fibronectin-treated chamber slides (Labtek) were transfected by a chloroquine-mediated DEAE-dextran procedure with plasmid DNAs derived from pooled transformants (2,000 transformants per pool) of murine El4cDNA library.

The CV1/EBNA cells transfected with the murine EL4cDNA pools were assayed for HVS13/Fc binding two days after transfection using [$^{125}$I] labeled goat anti-human IgG binding and slide autoradiography. Transfected cell monolayers were washed with binding medium (RPMI 1640 containing 1% bovine serum albumin and 50 mg/ml non-fat dry milk), then incubated with 1 μg/ml of HVS13/Fc for one hour at room temperature. Cells were washed, incubated with $^{125}$I-labeled goat anti-human IgG (New England nuclear, Cambridge, Mass.). Cells were washed twice with binding medium, three times with PBS, and fixed in PBS containing 2.5% gluteraldehyde for 30 minutes, washed twice more with PBS and air dried. The chamber slides were then dipped in Kodak GTNB-2 photographic emulsion and exposed for 3 days at 4° C. before developing.

Forty pools of approximately 2,000 cDNA each were transfected into CV1/EBNA cells. Two pools of cDNA were found to confer binding to HVS13/Fc protein. These pools were broken down to pools of 100 cDNAs, and subsequently to individual clones. Two single cDNA clones were isolated. These clones were transfected into CV1/EBNA to determine whether the protein encoded thereby conferred binding to both HVS13/Fc and mCTLA8/Fc. Both HVS/Fc and mCTLA8/Fc bound to CV1/EBNA cells transfected with the cloned cDNA, but not to cells transfected with empty vector. Control/Fc did not bind to either of them.

Sequencing of these clones found that they contained a 3.2 kb and 1.7 kb insert derived from same mRNA. The 3.2 kb clone contained an open reading frame of 2595 bp surrounded by 120 bp at the 5' noncoding sequence and 573 bp of 3' noncoding sequence. There were no in-frame stop codons upstream of the predicted initiator methionine, which is preceded by a purine residue (guanine) at −3 position, the most important indicator of a good translation initiation site (Kozak, *Mol. Cell. Biol.* 9:5134, 1989). It also has a guanine at +4 position, making it an optimal for translation initiation. The open reading frame is predicted to encode a type I transmembrane protein of 864 amino acids. The nucleotide and predicted amino acid sequence is shown in SEQ ID NOs:1 and 2.

Computer analysis indicated that the protein has an N-terminal signal peptide with a cleavage site between amino acid 31 and 32. The signal peptide is followed by a 291 amino acid extracellular domain, a 21 amino acid transmembrane domain, and a 521 amino acid cytoplasmic tail. There are eight potential N-linked glycosylation sites in the extracellular domain of the protein. The predicted molecular weight for this protein is 97.8 kilodaltons with an estimated isoelectric point of 4.85. Comparison of both nucleotide and amino acid sequences with the GenBank or EMBL databases found no significant homology with known nucleotide and protein sequences.

In order to determine the cellular and tissue distribution of IL-17R mRNA, poly (A)$^+$ RNA derived from various murine cell lines or tissues was examined by Northern blot analysis using the IL-17R cDNA as a probe. Filters containing poly(A)$^+$ RNA (2 μg per lane) from various tissues were purchased from Clontech (Palo Alto, Calif.). Polyadenylated RNA from various cells or cell lines were isolated, fractionated (2 μg per lane) on a 1% agarose formaldehyde gel, blotted onto Hybond nylon membrane (Amersham). Filters were probed with an anti-sense RNA riboprobe corresponding to the coding region of IL-17R cDNA. Hybridization was performed at 63° C. followed by three washings in 0.2%×SSC, 0.1% SDS at 68° C. Blots were exposed for 8 to 48 hr at −70° C.

The IL-17R probe hybridized to a single species of mRNA of approximately 3.7 kb in all tissues. Among the tissues examined, strong hybridizing signals were observed in spleen and kidney. Moderate signals were observed in lung and liver, and weaker signals in brain, heart, skeletal muscle and testes. Similar size mRNAs were detected in the following cells and cell lines: fetal liver epithelial cells (D11), fibroblast (3T3), rat intestinal epithelial cells (1CE6), splenic B cells, muscle cells (BB4), mast cells (H7), triple negative thymus cells (TN), pre-B cells (70Z/3), T cell hybridoma (EL4); and T cell clones 7C2 and D10. All the cell lines tested were found to express IL-17R mRNA, suggesting a ubiquitous expression of IL-17R message.

EXAMPLE 3

This example describes construction of a construct to express a soluble IL-17R/Flag® protein referred to as IL-17R/Flag. IL-17R/Flag® contains a leader sequence, and the region of IL-17R from amino acid 1 to amino acid 322 (SEQ ID NO:1), and the octapeptide referred to as Flag® (SEQ ID NO:3). The construct is prepared essentially as described for other soluble constructs, by ligating a DNA fragment encoding amino acids 1 through 322 of SEQ ID NO:1 (prepared as described in Example 4) into an appropriate expression vector which contains a suitable leader sequence. The resultant DNA construct is transfected into a suitable cell line such as the monkey kidney cell line CV-1/EBNA (ATCC CRL 10478). IL-17R/Flag® may be purified using a Flag® antibody affinity column, and analyzed for biological activity using any of the methods described herein.

EXAMPLE 4

This example describes construction of a IL-17R DNA construct to express a IL-17R/Fc fusion protein. A soluble form of IL-17R fused to the Fc region of human IgG1 was constructed in the mammalian expression vector pDC409 in the following way: A pair of oligonucleotide primers containing a sense sequence and an antisense sequence of IL-17R were synthesized. The sense primer contained a Sal I site at the 5' end of the cDNA and antisense primer contained a Bgl II site and contained the IL-17R truncated just before the transmembrane region and a stop codon. A 980 bp DNA fragment was amplified from IL-17R cDNA. The PCR product was cut with Sal I and Bgl II and used in a three way ligation with a fragment carrying the human IgG1 region cut with Bgl II and Not I into a plasmid (pDC409; see U.S. Ser. No. 08/235,397) previously cut with Sal I and Not I. The encoded insert contained the nucleotides encoding the amino acid sequence of residues 1 to 322 of IL-17R (SEQ ID NO:1). The sequence was confirmed by sequencing the whole region.

The IL-17R/Fc expression plasmids were transfected into CV-1/EBNA cells, and supernatants were collected for 1 week. The CTLA-8/Fc fusion proteins were purified on a protein A sepharose column (Pharmacia, Uppsala, Sweden) as described below. Protein concentration was determined by an enzyme-linked immunoadsorbent assay specific for the constant domain of human IgG1 and by BCA analysis (Pharmacia), and purity was confirmed by SDS-polyacrylamide gel electrophoresis analysis followed by silver stain of the gel.

EXAMPLE 5

This example describes purification of IL-17R fusion proteins. IL-17R/Fc fusion protein is purified by conventional methods using Protein A or Protein G chromatography. Approximately one liter of culture supernatant containing IL-17R/Fc fusion protein is purified by filtering mammalian cell supernatants (e.g., in a 0.45 m filter) and applying filtrate to a protein A/G antibody affinity column (Schleicher and Schuell, Keene, N.H.) at 4° C. at a flow rate of 80 ml/hr for a 1.5 cm×12.0 cm column. The column is washed with 0.5M NaCl in PBS until free protein is not detected in the wash buffer. Finally, the column is washed with PBS. Bound fusion protein is eluted from the column with 25 mM citrate buffer, pH 2.8, and brought to pH 7 with 500 mM Hepes buffer, pH 9.1.

A IL-17R fusion protein comprising Flag® may also be detected and/or purified using an antibody that binds Flag®, substantially as described in Hopp et al., Bio/Technology 6:1204 (1988). Biological activity is measured by inhibition of CTLA-8 activity in any biological assay which quantifies the co-stimulatory effect of CTLA-8, for example, as described in the Examples herein.

EXAMPLE 6

This example illustrates the preparation of monoclonal antibodies against IL-17R. Preparations of purified recombinant IL-17R, for example, or transfected cells expressing high levels of IL-17R, are employed to generate monoclonal antibodies against IL-17R using conventional techniques, such as those disclosed in U.S. Pat. No. 4,411,993. Such antibodies are likely to be useful in interfering with IL-17R binding to CTLA-8, as components of diagnostic or research assays for IL-17R, or in affinity purification of IL-17R.

To immunize rodents, IL-17R immunogen is emulsified in an adjuvant (such as complete or incomplete Freund's adjuvant, alum, or another adjuvant, such as Ribi adjuvant R700 (Ribi, Hamilton, Mont.), and injected in amounts ranging from 10-100 μg subcutaneously into a selected rodent, for example, BALB/c mice or Lewis rats. Ten days to three weeks days later, the immunized animals are boosted with additional immunogen and periodically boosted thereafter on a weekly, biweekly or every third week immunization schedule. Serum samples are periodically taken by retro-orbital bleeding or tail-tip excision for testing by dot-blot assay (antibody sandwich), ELISA (enzyme-linked immunosorbent assay), immunoprecipitation, or other suitable assays, including FACS analysis. Following detection of an appropriate antibody titer, positive animals are given an intravenous injection of antigen in saline. Three to four days later, the animals are sacrificed, splenocytes harvested, and fused to a murine myeloma cell line (e.g., NS1 or preferably Ag 8.653 [ATCC CRL 1580]). Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenocyte hybrids.

Hybridoma clones thus generated can be screened by ELISA for reactivity with IL-17R, for example, by adaptations of the techniques disclosed by Engvall et al., Immunochem. 8:871 (1971) and in U.S. Pat. No. 4,703,004. A preferred screening technique is the antibody capture technique described by Beckman et al., J. Immunol. 144:4212 (1990). Positive clones are then injected into the peritoneal cavities of syngeneic rodents to produce ascites containing high concentrations (>1 mg/ml) of anti-IL-17R monoclonal antibody. The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to IL-17R protein.

EXAMPLE 7

This example illustrates the ability of IL-17R to inhibit the proliferative response of T cells to mitogens. Lymphoid organs were harvested aseptically and cell suspension was created. Splenic and lymph node T cells were isolated from the cell suspension. The purity of the resulting splenic T cell preparations was routinely >95% CD3$^+$and <1% sIgM$^+$. Purified murine splenic T cells (2×10$^5$/well) were cultured with either 1% PHA or 1 μg/ml Con A, and a soluble IL-17R was titered into the assay. Proliferation was determined after 3 days with the addition of 1 μCi [$^3$H]thymidine. Secretion of cytokines (Interleukin-2) was determined for murine T cells cultured for 24 hr with 1 μg/ml of Con A in the presence or absence of 10 μg/ml of IL-17R.Fc or in the presence of a control Fc protein. IL-2 production was measured by ELISA and results expressed as ng/ml IL-2 produced.

Soluble IL-17R/Fc significantly inhibited the mitogen-induced proliferation of purified murine splenic T cells in a dose dependent manner, while a control Fc had no effect on the murine T cell proliferation. Complete inhibition of mitogen induced proliferation was observed at a soluble IL-17R.Fc concentration of 10 μg/ml. Analysis of IL-2 production by splenic T cells activated with Con A in the presence or absence of IL-17R.Fc in the culture revealed that addition of IL-17R.Fc to the T-cell culture inhibited IL-2 production to levels 8-9-fold lower than those observed in cultures containing media alone or media plus a control Fc protein. Similar results were observed when purified human T cells were used.

EXAMPLE 8

This example presents the isolation of a DNA encoding human IL-17R by cross species hybridization. A human peripheral blood lymphocyte library was prepared and screened substantially as described in U.S. Ser. No. 08/249, 189, using murine IL-17R DNA under moderately high stringency conditions. Several clones of varying length were obtained. Sequencing data indicated that the human IL-17R was approximately 76% identical to murine IL-17R at the nucleotide level. The nucleotide and predicted amino acid sequence of human IL-17R is shown in SEQ ID NOs:10 and 11. A plasmid (pGEMBL) containing DNA encoding the human IL-17 receptor (referred to as pGEMBL-HuIL-17R) in E. coli DH10, was deposited with the American Type Culture Collection, 12301 Parklawn Drive, Rockville, Md. 20852-1776, USA, on Jun. 5, 1995, under the conditions of the Budapest Treaty, and assigned accession number 69834.

The human IL-17R shared many features with the murine IL-17 R. Computer analysis indicated that the protein has an N-terminal signal peptide with a cleavage site between amino acid 27 and 28. The signal peptide is followed by a 293 amino acid extracellular domain, a 21 amino acid transmembrane domain, and a 525 amino acid cytoplasmic tail. Soluble IL-17R comprises the signal peptide and the extracellular domain (residues 1 to 320 of SEQ ID NO:1) or a fragment thereof. Alternatively, a different signal peptide can be substituted for the native signal peptide. A Type I Fc fusion protein (wherein DNA encoding the Fc region of an immunoglobulin molecule is fused to DNA encoding the IL-17R immediately before, and in place of, the DNA encoding the transmembrane region of the IL-17R) was prepared, substantially as described in Example 4. A soluble hIL-17R protein can be also expressed substantially as described in Example 3, or by any other method of preparing and expressing the extracellular domain of IL-17R or a fragment thereof.

EXAMPLE 9

This example presents the localization and fine mapping of the murine IL-17R gene. A panel of DNA samples from an interspecific cross that has been characterized for over 900 genetic markers throughout the genome was analyzed.

The genetic markers included in this map span between 50 and 80 centi-Morgans on each mouse autosome and the X chromosome (Chr) (Saunders and Seldin, *Genomics* 8:524, 1990; Watson et al., *Mammalian Genome* 2:158, 1992).

Initially, DNA from the two parental mice [C3H/HeJ-gld and (C3H/HeJ-gld x *Mus spretus*) F1] were digested with various restriction endonucleases and hybridized with the IL-17R cDNA probe to determine restriction fragment length variants (RFLVs) to allow haplotype analyses. Informative BglI RFLVs were detected: C3H/HeJ-gld, 10.0 kb; *Mus spretus*, 7.8 kb and 2.2 kb). In each of the backcross mice either the C3H/HeJ-gld parental band or all three bands (both *Mus spretus* bands and a half intensity C3H/HEJ-gld band) were observed indicating that a single locus was detected.

Comparison of the haplotype distribution of the IL-17R RFLVs indicated that this gene cosegregated in 111 of the 114 meiotic events examined with the Raf1 gene locus on mouse Chr 6. The best gene order (Bishop, *Genet. Epidemiol.* 2:349, 1985)±the standard deviation (Green, *In Genetics and Probability in Animal Breeding Experiments*. E. Green, ed.; Macmillan, New York, pp.77–113, 1981) was: (centromere) Raf1-2.6 cM±1.5 cM - IL-17R-2.5 cM±1.5 cM-Cd4.

EXAMPLE 10

This example demonstrates that soluble IL-17R suppresses rejection of organ grafts in vivo. Hearts from neonatal C57BL/6 (H-$2^b$) mice (less than 24 hours old) were transplanted into the ear pinnae of adult BALB/c (H-$2^d$) recipients substantially as described in U.S. Pat. No. 5,492,888, issued Feb. 20, 1996 (utilizing the method of Fulmer et al., *Am. J. Anat.* 113:273, 1963, modified as described by Trager et al., *Transplantation* 47:587, 1989, and Van Buren et al., *Transplant. Proc.* 15:2967, 1983). Survival of the transplanted hearts was assessed by visually inspecting the grafts for pulsatile activity, as determined by examining the ear-heart grafts of anesthetized recipients under a dissecting microscope with soft reflected light beginning on day 5 or 6 post transplant. The time of graft rejection was defined as the day after transplantation on which contractile activity ceased.

In one set of experiments, neonatal hearts were removed, rinsed with sterile PBS to remove excess blood, and placed into prepared ear pinnae. Recipient mice were given either soluble murine IL-17R/Fc (100 μg in 200 μl; see Example 4 herein) or rat IgG as a control, i.p. on days 0 through 3 post transplantation. In a second set of experiments, the recipient mice were injected with IL-17R or human IgG on days 0, 1 and 2; the quantity and route of injection were ass done previously. The results of these experiments are shown in Table 1.

TABLE 1

Effects of Soluble Murine IL-17R (smuIL-17R) on Neovascularized Heterotopic Cardiac Allograft Survival

|  | Treatment Group | Survival Time (days) | Median Survival Time ± S. D. |
| --- | --- | --- | --- |
| Experiment 1 | rat IgG | 11, 14, 14, 14 | 13 ± 1.5 |
|  | smuIL-17R | 19, 19, 19, 21 | 20 ± 1.0 |
| Experiment 2 | human IgG | 13, 13, 13, 15 | 14 ± 1.0 |
|  | smuIL-17R | 20, 20, 20, 20 | 20 ± 0.0 |

Table 1 shows that heart allografts survived approximately 13 days in individual control mice treated with rat IgG. When allograft recipients were given up to four daily injections of soluble IL-17R, graft survival was prolonged, with a median survival of 20, approximately seven days longer than the survival time of identical grafts in control mice. When a prolonged release of the IL-17R was obtained by encapsulating the soluble IL-17R in alginate beads, it was observed that a single administration of 100 μg soluble IL-17R prolonged graft survival in much the same manner as observed previously with soluble IL-17R in solution. These results demonstrate that soluble IL-17R suppresses rejection of grafted tissues.

EXAMPLE 11

This example demonstrates that DNA encoding soluble IL-17R will be useful in suppressing rejection of organ grafts in vivo. Hearts from neonatal C57BL/6(H-$2^b$) mice were transplanted into the ear pinnae of adult BALB/c (H-$2^d$) recipients as described in Example 10 above, except that the hearts were injected with 15 μl of PBS containing either IL-17R/Fc-encoding DNA (pDC409-IL-17R; Example 4) or control DNA (empty pDC409) at a concentration of about 1 mg/ml, into a ventricle. A 30 gauge needle was used, and care was taken to minimize trauma to the heart. The transfected hearts were then transplanted into BALB/c recipients and graft survival determined as described previously. Results are presented below in Table 2.

TABLE 2

Effects of Expression of Soluble Murine IL-17R by Cardiac Cells on Neovascularized Heterotopic Cardiac Allograft Survival

| Treatment Group | Survival Time (days) | Median Survival Time ± S. D. |
| --- | --- | --- |
| rat IgG | 13, 15, 15, 15, 18 | 15 ± 1.8 |
| smuIL-17R | 20, 25, 28, >60, >60 | ND* |

*ND: Not done; median survival time could not be calculated since two mice still show pulsatile grafts more than two months after transplantation.

Table 2 shows that heart allografts survived approximately 15 days in individual control mice transplanted with hearts transfected with empty vector. When the transplanted hearts were transfected with DNA encoding soluble IL-17R, graft survival was prolonged. For three of the five mice in this group, grafts survived on average approximately 24 days, nine days longer than the survival time of identical grafts in control mice. The grafts given the other two mice were still puslatile (i.e., had not been rejected) more than 60 days post transplant., and had apparently been accepted by the recipients. These results demonstrate that transfecting tissues to be grafted with DNA encoding soluble IL-17R ameliorates rejection of those tissues by the recipient.

5,869,286

We claim:

1. An isolated DNA selected from the group consisting of:
  (a) a DNA encoding a protein having an amino acid sequence of amino acids 1 through 322 of SEQ ID NO.: 2;
  (b) a DNA encoding a protein having an amino acid sequence of amino acids 1 through 320 of SEQ ID NO.: 10;
  (c) DNA molecules capable of hybridization to the DNA of (a) or (b) under stringent conditions, and which encode IL-17R that bind IL-17; and
  (d) fragments of the DNA molecules of (a), (b), or (c), which encode proteins comprising an extracellular domain of the mature proteins of SEQ ID NO:2 or SEQ ID NO:10, that bind L-17.

2. An isolated DNA selected from the group consisting of:
  (a) a DNA encoding a protein having an amino acid sequence of amino acids 1 through 322 of SEQ ID NO.: 2; and
  (b) a DNA encoding a protein having an amino acids sequence of amino acids 1 through 320 of SEQ ID NO.: 10.

3. An isolated DNA selected from the group consisting of:
  (a) a DNA encoding a protein having an amino acid sequence of amino acids 1 through 322 of SEQ ID NO.: 2;
  (b) a DNA encoding a protein having an amino acid sequence of amino acids 1 through 320 of SEQ ID NO.: 10; and
  (c) fragments of the DNA molecules of (a), or (b) which encode proteins comprising an extracellular domain of the mature proteins of SEQ ID NO:2 or SEQ ID NO:10, that bind IL-17.

4. A recombinant expression vector comprising a DNA sequence according to claim 1.

5. A recombinant expression vector according to claim 4 that expresses a soluble IL-17R.

6. A recombinant expression vector comprising a DNA sequence according to claim 3.

7. A host cell transformed or transfected with an expression vector according to claim 4.

8. A host cell transformed or transfected with an expression vector according to claim 5.

9. A host cell transformed or transfected with an expression vector according to claim 6.

10. A process for preparing an IL-17R protein, comprising culturing a host cell according to claim 7 under conditions promoting expression and recovering the IL-17R.

11. A process for preparing an IL-17R protein, comprising culturing a host cell according to claim 8 under conditions promoting expression and recovering the IL-17R.

12. A process for preparing an IL-17R protein, comprising culturing a host cell according to claim 9 under conditions promoting expression and recovering the IL-17R.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 3288 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Mouse
        ( B ) STRAIN: HVS13 receptor ( i x ) FEATURE:
        ( A ) NAME/KEY: CDS
        ( B ) LOCATION: 121..2715

( x i ) SEQUENCE DESCRIPTION: SEQ ID NO:1:

```
GTCGACTGGA ACGAGACGAC CTGCTGCCGA CGAGCGCCAG TCCTCGGCCG GGAAAGCCAT        60

CGCGGGCCCT CGCTGTCGCG CGGAGCCAGC TGCGAGCGCT CCGCGACCGG GCCGAGGGCT       120

ATG GCG ATT CGG CGC TGC TGG CCA CGG GTC GTC CCC GGG CCC GCG CTG        168
Met Ala Ile Arg Arg Cys Trp Pro Arg Val Val Pro Gly Pro Ala Leu
 1               5                  10                  15

GGA TGG CTG CTT CTG CTG CTG AAC GTT CTG GCC CCG GGC CGC GCC TCC        216
Gly Trp Leu Leu Leu Leu Leu Asn Val Leu Ala Pro Gly Arg Ala Ser
             20                  25                  30

CCG CGC CTC CTC GAC TTC CCG GCT CCG GTC TGC GCG CAG GAG GGG CTG        264
Pro Arg Leu Leu Asp Phe Pro Ala Pro Val Cys Ala Gln Glu Gly Leu
         35                  40                  45

AGC TGC AGA GTC AAG AAT AGT ACT TGT CTG GAT GAC AGC TGG ATC CAC        312
Ser Cys Arg Val Lys Asn Ser Thr Cys Leu Asp Asp Ser Trp Ile His
     50                  55                  60

CCC AAA AAC CTG ACC CCG TCT TCC CCA AAA AAC ATC TAT ATC AAT CTT        360
Pro Lys Asn Leu Thr Pro Ser Ser Pro Lys Asn Ile Tyr Ile Asn Leu
 65                  70                  75                  80

AGT GTT TCC TCT ACC CAG CAC GGA GAA TTA GTC CCT GTG TTG CAT GTT        408
Ser Val Ser Ser Thr Gln His Gly Glu Leu Val Pro Val Leu His Val
                 85                  90                  95

GAG TGG ACC CTG CAG ACA GAT GCC AGC ATC CTG TAC CTC GAG GGT GCA        456
Glu Trp Thr Leu Gln Thr Asp Ala Ser Ile Leu Tyr Leu Glu Gly Ala
            100                 105                 110

GAG CTG TCC GTC CTG CAG CTG AAC ACC AAT GAG CGG CTG TGT GTC AAG        504
Glu Leu Ser Val Leu Gln Leu Asn Thr Asn Glu Arg Leu Cys Val Lys
        115                 120                 125

TTC CAG TTT CTG TCC ATG CTG CAG CAT CAC CGT AAG CGG TGG CGG TTT        552
Phe Gln Phe Leu Ser Met Leu Gln His His Arg Lys Arg Trp Arg Phe
    130                 135                 140

TCC TTC AGC CAC TTT GTG GTA GAT CCT GGC CAG GAG TAT GAA GTG ACT        600
Ser Phe Ser His Phe Val Val Asp Pro Gly Gln Glu Tyr Glu Val Thr
145                 150                 155                 160

GTT CAC CAC CTG CCG AAG CCC ATC CCT GAT GGG GAC CCA AAC CAC AAA        648
Val His His Leu Pro Lys Pro Ile Pro Asp Gly Asp Pro Asn His Lys
                165                 170                 175
```

| | | | | | | | | | | | | | | | | |
|---|---|---|---|---|---|---|---|---|---|---|---|---|---|---|---|---|
| TCC | AAG | ATC | ATC | TTT | GTG | CCT | GAC | TGT | GAG | GAC | AGC | AAG | ATG | AAG | ATG | 696 |
| Ser | Lys | Ile | Ile 180 | Phe | Val | Pro | Asp | Cys 185 | Glu | Asp | Ser | Lys | Met 190 | Lys | Met | |
| ACT | ACC | TCA | TGC | GTG | AGC | TCA | GGC | AGC | CTT | TGG | GAT | CCC | AAC | ATC | ACT | 744 |
| Thr | Thr | Ser 195 | Cys | Val | Ser | Ser | Gly | Ser 200 | Leu | Trp | Asp | Pro 205 | Asn | Ile | Thr | |
| GTG | GAG | ACC | TTG | GAC | ACA | CAG | CAT | CTG | CGA | GTG | GAC | TTC | ACC | CTG | TGG | 792 |
| Val | Glu 210 | Thr | Leu | Asp | Thr | Gln 215 | His | Leu | Arg | Val | Asp 220 | Phe | Thr | Leu | Trp | |
| AAT | GAA | TCC | ACC | CCC | TAC | CAG | GTC | CTG | CTG | GAA | AGT | TTC | TCC | GAC | TCA | 840 |
| Asn 225 | Glu | Ser | Thr | Pro | Tyr 230 | Gln | Val | Leu | Leu | Glu 235 | Ser | Phe | Ser | Asp | Ser 240 | |
| GAG | AAC | CAC | AGC | TGC | TTT | GAT | GTC | GTT | AAA | CAA | ATA | TTT | GCG | CCC | AGG | 888 |
| Glu | Asn | His | Ser | Cys 245 | Phe | Asp | Val | Val | Lys 250 | Gln | Ile | Phe | Ala | Pro 255 | Arg | |
| CAA | GAA | GAA | TTC | CAT | CAG | CGA | GCT | AAT | GTC | ACA | TTC | ACT | CTA | AGC | AAG | 936 |
| Gln | Glu | Glu | Phe 260 | His | Gln | Arg | Ala | Asn 265 | Val | Thr | Phe | Thr | Leu 270 | Ser | Lys | |
| TTT | CAC | TGG | TGC | TGC | CAT | CAC | CAC | GTG | CAG | GTC | CAG | CCC | TTC | TTC | AGC | 984 |
| Phe | His | Trp 275 | Cys | Cys | His | His | His 280 | Val | Gln | Val | Gln | Pro 285 | Phe | Phe | Ser | |
| AGC | TGC | CTA | AAT | GAC | TGT | TTG | AGA | CAC | GCT | GTG | ACT | GTG | CCC | TGC | CCA | 1032 |
| Ser | Cys 290 | Leu | Asn | Asp | Cys | Leu 295 | Arg | His | Ala | Val | Thr 300 | Val | Pro | Cys | Pro | |
| GTA | ATC | TCA | AAT | ACC | ACA | GTT | CCC | AAG | CCA | GTT | GCA | GAC | TAC | ATT | CCC | 1080 |
| Val 305 | Ile | Ser | Asn | Thr | Thr 310 | Val | Pro | Lys | Pro | Val 315 | Ala | Asp | Tyr | Ile | Pro 320 | |
| CTG | TGG | GTG | TAT | GGC | CTC | ATC | ACA | CTC | ATC | GCC | ATT | CTG | CTG | GTG | GGA | 1128 |
| Leu | Trp | Val | Tyr | Gly 325 | Leu | Ile | Thr | Leu | Ile 330 | Ala | Ile | Leu | Leu | Val 335 | Gly | |
| TCT | GTC | ATC | GTG | CTG | ATC | ATC | TGT | ATG | ACC | TGG | AGG | CTT | TCT | GGC | GCC | 1176 |
| Ser | Val | Ile | Val 340 | Leu | Ile | Ile | Cys | Met 345 | Thr | Trp | Arg | Leu | Ser 350 | Gly | Ala | |
| GAT | CAA | GAG | AAA | CAT | GGT | GAT | GAC | TCC | AAA | ATC | AAT | GGC | ATC | TTG | CCC | 1224 |
| Asp | Gln | Glu | Lys 355 | His | Gly | Asp | Asp | Ser 360 | Lys | Ile | Asn | Gly | Ile 365 | Leu | Pro | |
| GTA | GCA | GAC | CTG | ACT | CCC | CCA | CCC | CTG | AGG | CCC | AGG | AAG | GTC | TGG | ATC | 1272 |
| Val | Ala 370 | Asp | Leu | Thr | Pro | Pro 375 | Pro | Leu | Arg | Pro | Arg 380 | Lys | Val | Trp | Ile | |
| GTC | TAC | TCG | GCC | GAC | CAC | CCC | CTC | TAT | GTG | GAG | GTG | GTC | CTA | AAG | TTC | 1320 |
| Val 385 | Tyr | Ser | Ala | Asp | His 390 | Pro | Leu | Tyr | Val | Glu 395 | Val | Val | Leu | Lys | Phe 400 | |
| GCC | CAG | TTC | CTG | ATC | ACT | GCC | TGT | GGC | ACT | GAA | GTA | GCC | CTT | GAC | CTC | 1368 |
| Ala | Gln | Phe | Leu | Ile 405 | Thr | Ala | Cys | Gly | Thr 410 | Glu | Val | Ala | Leu | Asp 415 | Leu | |
| CTG | GAA | GAG | CAG | GTT | ATC | TCT | GAG | GTG | GGG | GTC | ATG | ACC | TGG | GTG | AGC | 1416 |
| Leu | Glu | Glu | Gln 420 | Val | Ile | Ser | Glu | Val 425 | Gly | Val | Met | Thr | Trp 430 | Val | Ser | |
| CGA | CAG | AAG | CAG | GAG | ATG | GTG | GAG | AGC | AAC | TCC | AAA | ATC | ATC | ATC | CTG | 1464 |
| Arg | Gln | Lys 435 | Gln | Glu | Met | Val | Glu 440 | Ser | Asn | Ser | Lys | Ile 445 | Ile | Ile | Leu | |
| TGT | TCC | CGA | GGC | ACC | CAA | GCA | AAG | TGG | AAA | GCT | ATC | TTG | GGT | TGG | GCT | 1512 |
| Cys | Ser | Arg 450 | Gly | Thr | Gln | Ala | Lys 455 | Trp | Lys | Ala | Ile | Leu 460 | Gly | Trp | Ala | |
| GAG | CCT | GCT | GTC | CAG | CTA | CGG | TGT | GAC | CAC | TGG | AAG | CCT | GCT | GGG | GAC | 1560 |
| Glu | Pro | Ala | Val | Gln 470 | Leu | Arg | Cys | Asp | His 475 | Trp | Lys | Pro | Ala | Gly 480 | Asp | |
| | | | | | | | | | | | | | | | | |
| CTT | TTC | ACT | GCA | GCC | ATG | AAC | ATG | ATC | CTG | CCA | GAC | TTC | AAG | AGG | CCA | 1608 |
| Leu | Phe | Thr | Ala 485 | Ala | Met | Asn | Met | Ile 490 | Leu | Pro | Asp | Phe | Lys 495 | Arg | Pro | |

(Note: row 465 label for Glu Pro Ala Val appears at position 465 on the left.)

| | | | | | | | | | | | | | | | | |
|---|---|---|---|---|---|---|---|---|---|---|---|---|---|---|---|---|
| GCC | TGC | TTC | GGC | ACC | TAC | GTT | GTT | TGC | TAC | TTC | AGT | GGC | ATC | TGT | AGT | 1656 |
| Ala | Cys | Phe | Gly | Thr | Tyr | Val | Val | Cys | Tyr | Phe | Ser | Gly | Ile | Cys | Ser | |
| | | | 500 | | | | 505 | | | | | 510 | | | | |
| GAG | AGG | GAT | GTC | CCC | GAC | CTC | TTC | AAC | ATC | ACC | TCC | AGG | TAC | CCA | CTC | 1704 |
| Glu | Arg | Asp | Val | Pro | Asp | Leu | Phe | Asn | Ile | Thr | Ser | Arg | Tyr | Pro | Leu | |
| | | 515 | | | | | 520 | | | | | 525 | | | | |
| ATG | GAC | AGA | TTT | GAG | GAG | GTT | TAC | TTC | CGG | ATC | CAG | GAC | CTG | GAG | ATG | 1752 |
| Met | Asp | Arg | Phe | Glu | Glu | Val | Tyr | Phe | Arg | Ile | Gln | Asp | Leu | Glu | Met | |
| | 530 | | | | | 535 | | | | | 540 | | | | | |
| TTT | GAA | CCC | GGC | CGG | ATG | CAC | CAT | GTC | AGA | GAG | CTC | ACA | GGG | GAC | AAT | 1800 |
| Phe | Glu | Pro | Gly | Arg | Met | His | His | Val | Arg | Glu | Leu | Thr | Gly | Asp | Asn | |
| 545 | | | | | 550 | | | | | 555 | | | | | 560 | |
| TAC | CTG | CAG | AGC | CCT | AGT | GGC | CGG | CAG | CTC | AAG | GAG | GCT | GTG | CTT | AGG | 1848 |
| Tyr | Leu | Gln | Ser | Pro | Ser | Gly | Arg | Gln | Leu | Lys | Glu | Ala | Val | Leu | Arg | |
| | | | | 565 | | | | | 570 | | | | | 575 | | |
| TTC | CAG | GAG | TGG | CAA | ACC | CAG | TGC | CCC | GAC | TGG | TTC | GAG | CGT | GAG | AAC | 1896 |
| Phe | Gln | Glu | Trp | Gln | Thr | Gln | Cys | Pro | Asp | Trp | Phe | Glu | Arg | Glu | Asn | |
| | | | 580 | | | | | 585 | | | | | 590 | | | |
| CTC | TGC | TTA | GCT | GAT | GGC | CAA | GAT | CTT | CCC | TCC | CTG | GAT | GAA | GAA | GTG | 1944 |
| Leu | Cys | Leu | Ala | Asp | Gly | Gln | Asp | Leu | Pro | Ser | Leu | Asp | Glu | Glu | Val | |
| | 595 | | | | | 600 | | | | | 605 | | | | | |
| TTT | GAA | GAC | CCA | CTG | CTG | CCA | CCA | GGG | GGA | GGA | ATT | GTC | AAA | CAG | CAG | 1992 |
| Phe | Glu | Asp | Pro | Leu | Leu | Pro | Pro | Gly | Gly | Gly | Ile | Val | Lys | Gln | Gln | |
| 610 | | | | | 615 | | | | | 620 | | | | | | |
| CCC | CTG | GTG | CGG | GAA | CTC | CCA | TCT | GAC | GGC | TGC | CTT | GTG | GTA | GAT | GTC | 2040 |
| Pro | Leu | Val | Arg | Glu | Leu | Pro | Ser | Asp | Gly | Cys | Leu | Val | Val | Asp | Val | |
| 625 | | | | | 630 | | | | | 635 | | | | | 640 | |
| TGT | GTC | AGT | GAG | GAA | GAA | AGT | AGA | ATG | GCA | AAG | CTG | GAC | CCT | CAG | CTA | 2088 |
| Cys | Val | Ser | Glu | Glu | Glu | Ser | Arg | Met | Ala | Lys | Leu | Asp | Pro | Gln | Leu | |
| | | | | 645 | | | | | 650 | | | | | 655 | | |
| TGG | CCA | CAG | AGA | GAG | CTA | GTG | GCT | CAC | ACC | CTC | CAA | AGC | ATG | GTG | CTG | 2136 |
| Trp | Pro | Gln | Arg | Glu | Leu | Val | Ala | His | Thr | Leu | Gln | Ser | Met | Val | Leu | |
| | | | 660 | | | | | 665 | | | | | 670 | | | |
| CCA | GCA | GAG | CAG | GTC | CCT | GCA | GCT | CAT | GTG | GTG | GAG | CCT | CTC | CAT | CTC | 2184 |
| Pro | Ala | Glu | Gln | Val | Pro | Ala | Ala | His | Val | Val | Glu | Pro | Leu | His | Leu | |
| | | 675 | | | | | 680 | | | | | 685 | | | | |
| CCA | GAC | GGC | AGT | GGA | GCA | GCT | GCC | CAG | CTG | CCC | ATG | ACA | GAG | GAC | AGC | 2232 |
| Pro | Asp | Gly | Ser | Gly | Ala | Ala | Ala | Gln | Leu | Pro | Met | Thr | Glu | Asp | Ser | |
| | 690 | | | | | 695 | | | | | 700 | | | | | |
| GAG | GCT | TGC | CCG | CTG | CTG | GGG | GTC | CAG | AGG | AAC | AGC | ATC | CTT | TGC | CTC | 2280 |
| Glu | Ala | Cys | Pro | Leu | Leu | Gly | Val | Gln | Arg | Asn | Ser | Ile | Leu | Cys | Leu | |
| 705 | | | | | 710 | | | | | 715 | | | | | 720 | |
| CCC | GTG | GAC | TCA | GAT | GAC | TTG | CCA | CTC | TGT | AGC | ACC | CCA | ATG | ATG | TCA | 2328 |
| Pro | Val | Asp | Ser | Asp | Asp | Leu | Pro | Leu | Cys | Ser | Thr | Pro | Met | Met | Ser | |
| | | | | 725 | | | | | 730 | | | | | 735 | | |
| CCT | GAC | CAC | CTC | CAA | GGC | GAT | GCA | AGA | GAG | CAG | CTA | GAA | AGC | CTA | ATG | 2376 |
| Pro | Asp | His | Leu | Gln | Gly | Asp | Ala | Arg | Glu | Gln | Leu | Glu | Ser | Leu | Met | |
| | | | 740 | | | | | 745 | | | | | 750 | | | |
| CTC | TCG | GTG | CTG | CAG | CAG | AGC | CTG | AGT | GGA | CAG | CCC | CTG | GAG | AGC | TGG | 2424 |
| Leu | Ser | Val | Leu | Gln | Gln | Ser | Leu | Ser | Gly | Gln | Pro | Leu | Glu | Ser | Trp | |
| | | 755 | | | | | 760 | | | | | 765 | | | | |
| CCG | AGG | CCA | GAG | GTG | GTC | CTC | GAG | GGC | TGC | ACA | CCC | TCT | GAG | GAG | GAG | 2472 |
| Pro | Arg | Pro | Glu | Val | Val | Leu | Glu | Gly | Cys | Thr | Pro | Ser | Glu | Glu | Glu | |
| | 770 | | | | | 775 | | | | | 780 | | | | | |
| CAG | CGG | CAG | TCG | GTG | CAG | TCG | GAC | CAG | GGC | TAC | ATC | TCC | AGG | AGC | TCC | 2520 |
| Gln | Arg | Gln | Ser | Val | Gln | Ser | Asp | Gln | Gly | Tyr | Ile | Ser | Arg | Ser | Ser | |
| 785 | | | | | 790 | | | | | 795 | | | | | 800 | |
| CCG | CAG | CCC | CCC | GAG | TGG | CTC | ACG | GAG | GAG | GAA | GAG | CTA | GAA | CTG | GGT | 2568 |
| Pro | Gln | Pro | Pro | Glu | Trp | Leu | Thr | Glu | Glu | Glu | Glu | Leu | Glu | Leu | Gly | |
| | | | | 805 | | | | | 810 | | | | | 815 | | |

| | | | | | | | | | | | | | | | | |
|---|---|---|---|---|---|---|---|---|---|---|---|---|---|---|---|---|
| GAG | CCC | GTT | GAG | TCT | CTC | TCT | CCT | GAG | GAA | CTA | CGG | AGC | CTG | AGG | AAG | 2616 |
| Glu | Pro | Val | Glu | Ser | Leu | Ser | Pro | Glu | Glu | Leu | Arg | Ser | Leu | Arg | Lys | |
| | | | 820 | | | | | 825 | | | | | 830 | | | |
| CTC | CAG | AGG | CAG | CTT | TTC | TTC | TGG | GAG | CTC | GAG | AAG | AAC | CCT | GGC | TGG | 2664 |
| Leu | Gln | Arg | Gln | Leu | Phe | Phe | Trp | Glu | Leu | Glu | Lys | Asn | Pro | Gly | Trp | |
| | | 835 | | | | | 840 | | | | | 845 | | | | |
| AAC | AGC | TTG | GAG | CCA | CGG | AGA | CCC | ACC | CCA | GAA | GAG | CAG | AAT | CCC | TCC | 2712 |
| Asn | Ser | Leu | Glu | Pro | Arg | Arg | Pro | Thr | Pro | Glu | Glu | Gln | Asn | Pro | Ser | |
| | 850 | | | | | 855 | | | | | 860 | | | | | |
| TAG | GCCTCCTGAG | CCTGCTACTT | AAGAGGGTGT | ATATTGTACT | CTGTGTGTGC | | | | | | | | | | | 2765 |
| * | | | | | | | | | | | | | | | | |
| 865 | | | | | | | | | | | | | | | | |
| GTGCGTGTGT | GTGTGTGTGT | GTGTGTGTGT | GTGCGTGTGT | GTGTGTGTGT | GTGTGTGTGT | | | | | | | | | | | 2825 |
| GTGTGTGTAG | TGCCCGGCTT | AGAAATGTGA | ACATCTGAAT | CTGACATAGT | GTTGTATACC | | | | | | | | | | | 2885 |
| TGAAGTCCCA | GCACTTGGGA | ACTGAGACTT | GATGATCTCC | TGAAGCCAGG | TGTTCAGGGC | | | | | | | | | | | 2945 |
| CAGTGTGAAA | ACATAGCAAG | ACCTCAGAGA | AATCAATGCA | GACATCTTGG | TACTGATCCC | | | | | | | | | | | 3005 |
| TAAACACACC | CCTTTCCCTG | ATAACCCGAC | ATGAGCATCT | GGTCATCATT | GCACAAGAAT | | | | | | | | | | | 3065 |
| CCACAGCCCG | TTCCCAGAGC | TCATAGCCAA | GTGTGTTGCT | CATTCCTTGA | ATATTTATTC | | | | | | | | | | | 3125 |
| TGTACCTACT | ATTCATCAGA | CATTTGGAAT | TCAAAAACAA | GTTACATGAC | ACAGCCTTAG | | | | | | | | | | | 3185 |
| CCACTAAGAA | GCTTAAAATT | CGGTAAGGAT | GTAAAATTAG | CCAGGATGAA | TAGAGGGCTG | | | | | | | | | | | 3245 |
| CTGCCCTGGC | TGCAGAAGAG | CAGGTCGTCT | CGTTCCAGTC | GAC | | | | | | | | | | | | 3288 |

(2) INFORMATION FOR SEQ ID NO:2:

(i) SEQUENCE CHARACTERISTICS:
        (A) LENGTH: 864 amino acids
        (B) TYPE: amino acid
        (D) TOPOLOGY: linear (ii) MOLECULE TYPE: protein (xi) SEQUENCE DESCRIPTION: SEQ ID NO:2:

| | | | | | | | | | | | | | | |
|---|---|---|---|---|---|---|---|---|---|---|---|---|---|---|
| Met | Ala | Ile | Arg | Arg | Cys | Trp | Pro | Arg | Val | Val | Pro | Gly | Pro | Ala | Leu |
| 1 | | | | 5 | | | | | 10 | | | | | 15 | |
| Gly | Trp | Leu | Leu | Leu | Leu | Leu | Asn | Val | Leu | Ala | Pro | Gly | Arg | Ala | Ser |
| | | | | 20 | | | | | 25 | | | | | 30 | |
| Pro | Arg | Leu | Leu | Asp | Phe | Pro | Ala | Pro | Val | Cys | Ala | Gln | Glu | Gly | Leu |
| | | | 35 | | | | | 40 | | | | | 45 | | |
| Ser | Cys | Arg | Val | Lys | Asn | Ser | Thr | Cys | Leu | Asp | Asp | Ser | Trp | Ile | His |
| | | 50 | | | | | 55 | | | | | 60 | | | |
| Pro | Lys | Asn | Leu | Thr | Pro | Ser | Ser | Pro | Lys | Asn | Ile | Tyr | Ile | Asn | Leu |
| 65 | | | | | 70 | | | | | 75 | | | | | 80 |
| Ser | Val | Ser | Ser | Thr | Gln | His | Gly | Glu | Leu | Val | Pro | Val | Leu | His | Val |
| | | | | 85 | | | | | 90 | | | | | 95 | |
| Glu | Trp | Thr | Leu | Gln | Thr | Asp | Ala | Ser | Ile | Leu | Tyr | Leu | Glu | Gly | Ala |
| | | | | 100 | | | | | 105 | | | | | 110 | |
| Glu | Leu | Ser | Val | Leu | Gln | Leu | Asn | Thr | Asn | Glu | Arg | Leu | Cys | Val | Lys |
| | | | 115 | | | | | 120 | | | | | 125 | | |
| Phe | Gln | Phe | Leu | Ser | Met | Leu | Gln | His | His | Arg | Lys | Arg | Trp | Arg | Phe |
| | | 130 | | | | | 135 | | | | | 140 | | | |
| Ser | Phe | Ser | His | Phe | Val | Val | Asp | Pro | Gly | Gln | Glu | Tyr | Glu | Val | Thr |
| 145 | | | | | 150 | | | | | 155 | | | | | 160 |
| Val | His | His | Leu | Pro | Lys | Pro | Ile | Pro | Asp | Gly | Asp | Pro | Asn | His | Lys |
| | | | | 165 | | | | | 170 | | | | | 175 | |
| Ser | Lys | Ile | Ile | Phe | Val | Pro | Asp | Cys | Glu | Asp | Ser | Lys | Met | Lys | Met |

-continued

```
                    180                        185                         190
Thr  Thr  Ser  Cys  Val  Ser  Ser  Gly  Ser  Leu  Trp  Asp  Pro  Asn  Ile  Thr
               195                 200                 205

Val  Glu  Thr  Leu  Asp  Thr  Gln  His  Leu  Arg  Val  Asp  Phe  Thr  Leu  Trp
     210                 215                 220

Asn  Glu  Ser  Thr  Pro  Tyr  Gln  Val  Leu  Leu  Glu  Ser  Phe  Ser  Asp  Ser
225                      230                 235                           240

Glu  Asn  His  Ser  Cys  Phe  Asp  Val  Val  Lys  Gln  Ile  Phe  Ala  Pro  Arg
                    245                 250                           255

Gln  Glu  Glu  Phe  His  Gln  Arg  Ala  Asn  Val  Thr  Phe  Thr  Leu  Ser  Lys
               260                 265                      270

Phe  His  Trp  Cys  Cys  His  His  His  Val  Gln  Val  Gln  Pro  Phe  Phe  Ser
          275                      280                 285

Ser  Cys  Leu  Asn  Asp  Cys  Leu  Arg  His  Ala  Val  Thr  Val  Pro  Cys  Pro
     290                 295                 300

Val  Ile  Ser  Asn  Thr  Thr  Val  Pro  Lys  Pro  Val  Ala  Asp  Tyr  Ile  Pro
305                      310                 315                           320

Leu  Trp  Val  Tyr  Gly  Leu  Ile  Thr  Leu  Ile  Ala  Ile  Leu  Leu  Val  Gly
                    325                 330                 335

Ser  Val  Ile  Val  Leu  Ile  Ile  Cys  Met  Thr  Trp  Arg  Leu  Ser  Gly  Ala
               340                 345                 350

Asp  Gln  Glu  Lys  His  Gly  Asp  Asp  Ser  Lys  Ile  Asn  Gly  Ile  Leu  Pro
               355                 360                 365

Val  Ala  Asp  Leu  Thr  Pro  Pro  Leu  Arg  Pro  Arg  Lys  Val  Trp  Ile
     370                 375                 380

Val  Tyr  Ser  Ala  Asp  His  Pro  Leu  Tyr  Val  Glu  Val  Val  Leu  Lys  Phe
385                      390                 395                           400

Ala  Gln  Phe  Leu  Ile  Thr  Ala  Cys  Gly  Thr  Glu  Val  Ala  Leu  Asp  Leu
               405                 410                 415

Leu  Glu  Glu  Gln  Val  Ile  Ser  Glu  Val  Gly  Val  Met  Thr  Trp  Val  Ser
               420                 425                 430

Arg  Gln  Lys  Gln  Glu  Met  Val  Glu  Ser  Asn  Ser  Lys  Ile  Ile  Ile  Leu
          435                 440                 445

Cys  Ser  Arg  Gly  Thr  Gln  Ala  Lys  Trp  Lys  Ala  Ile  Leu  Gly  Trp  Ala
     450                 455                 460

Glu  Pro  Ala  Val  Gln  Leu  Arg  Cys  Asp  His  Trp  Lys  Pro  Ala  Gly  Asp
465                 470                 475                           480

Leu  Phe  Thr  Ala  Ala  Met  Asn  Met  Ile  Leu  Pro  Asp  Phe  Lys  Arg  Pro
               485                      490                 495

Ala  Cys  Phe  Gly  Thr  Tyr  Val  Val  Cys  Tyr  Phe  Ser  Gly  Ile  Cys  Ser
               500                 505                 510

Glu  Arg  Asp  Val  Pro  Asp  Leu  Phe  Asn  Ile  Thr  Ser  Arg  Tyr  Pro  Leu
          515                 520                 525

Met  Asp  Arg  Phe  Glu  Glu  Val  Tyr  Phe  Arg  Ile  Gln  Asp  Leu  Glu  Met
     530                 535                 540

Phe  Glu  Pro  Gly  Arg  Met  His  His  Val  Arg  Glu  Leu  Thr  Gly  Asp  Asn
545                      550                 555                           560

Tyr  Leu  Gln  Ser  Pro  Ser  Gly  Arg  Gln  Leu  Lys  Glu  Ala  Val  Leu  Arg
                    565                 570                 575

Phe  Gln  Glu  Trp  Gln  Thr  Gln  Cys  Pro  Asp  Trp  Phe  Glu  Arg  Glu  Asn
               580                 585                 590

Leu  Cys  Leu  Ala  Asp  Gly  Gln  Asp  Leu  Pro  Ser  Leu  Asp  Glu  Glu  Val
          595                 600                 605
```

| | | | | | | | | | | | | | | |
|---|---|---|---|---|---|---|---|---|---|---|---|---|---|---|
| Phe | Glu | Asp | Pro | Leu | Leu | Pro | Pro | Gly | Gly | Gly | Ile | Val | Lys | Gln | Gln |
| | 610 | | | | 615 | | | | | 620 | | | | |
| Pro | Leu | Val | Arg | Glu | Leu | Pro | Ser | Asp | Gly | Cys | Leu | Val | Val | Asp | Val |
| 625 | | | | | 630 | | | | | 635 | | | | | 640 |
| Cys | Val | Ser | Glu | Glu | Ser | Arg | Met | Ala | Lys | Leu | Asp | Pro | Gln | Leu |
| | | | | 645 | | | | | 650 | | | | | 655 |
| Trp | Pro | Gln | Arg | Glu | Leu | Val | Ala | His | Thr | Leu | Gln | Ser | Met | Val | Leu |
| | | | 660 | | | | | 665 | | | | | 670 | | |
| Pro | Ala | Glu | Gln | Val | Pro | Ala | Ala | His | Val | Val | Glu | Pro | Leu | His | Leu |
| | | 675 | | | | | 680 | | | | | 685 | | | |
| Pro | Asp | Gly | Ser | Gly | Ala | Ala | Ala | Gln | Leu | Pro | Met | Thr | Glu | Asp | Ser |
| | 690 | | | | | 695 | | | | | 700 | | | | |
| Glu | Ala | Cys | Pro | Leu | Leu | Gly | Val | Gln | Arg | Asn | Ser | Ile | Leu | Cys | Leu |
| 705 | | | | | 710 | | | | | 715 | | | | | 720 |
| Pro | Val | Asp | Ser | Asp | Asp | Leu | Pro | Leu | Cys | Ser | Thr | Pro | Met | Met | Ser |
| | | | | 725 | | | | | 730 | | | | | 735 | |
| Pro | Asp | His | Leu | Gln | Gly | Asp | Ala | Arg | Glu | Gln | Leu | Glu | Ser | Leu | Met |
| | | | 740 | | | | | 745 | | | | | 750 | | |
| Leu | Ser | Val | Leu | Gln | Gln | Ser | Leu | Ser | Gly | Gln | Pro | Leu | Glu | Ser | Trp |
| | | 755 | | | | | 760 | | | | | 765 | | | |
| Pro | Arg | Pro | Glu | Val | Val | Leu | Glu | Gly | Cys | Thr | Pro | Ser | Glu | Glu | Glu |
| | 770 | | | | | 775 | | | | | 780 | | | | |
| Gln | Arg | Gln | Ser | Val | Gln | Ser | Asp | Gln | Gly | Tyr | Ile | Ser | Arg | Ser | Ser |
| 785 | | | | | 790 | | | | | 795 | | | | | 800 |
| Pro | Gln | Pro | Pro | Glu | Trp | Leu | Thr | Glu | Glu | Glu | Leu | Glu | Leu | Gly |
| | | | | 805 | | | | | 810 | | | | | 815 |
| Glu | Pro | Val | Glu | Ser | Leu | Ser | Pro | Glu | Glu | Leu | Arg | Ser | Leu | Arg | Lys |
| | | | 820 | | | | | 825 | | | | | 830 | | |
| Leu | Gln | Arg | Gln | Leu | Phe | Phe | Trp | Glu | Leu | Glu | Lys | Asn | Pro | Gly | Trp |
| | | 835 | | | | | 840 | | | | | 845 | | | |
| Asn | Ser | Leu | Glu | Pro | Arg | Arg | Pro | Thr | Pro | Glu | Glu | Gln | Asn | Pro | Ser |
| | 850 | | | | | 855 | | | | | 860 | | | | |
| *
865 | | | | | | | | | | | | | | | |

( 2 ) INFORMATION FOR SEQ ID NO:3:

( i ) SEQUENCE CHARACTERISTICS:
    ( A ) LENGTH: 8 amino acids
    ( B ) TYPE: amino acid
    ( C ) STRANDEDNESS: Not Relevant
    ( D ) TOPOLOGY: linear ( i i ) MOLECULE TYPE: peptide ( v i i ) IMMEDIATE SOURCE:
    ( B ) CLONE: FLAG_peptide ( x i ) SEQUENCE DESCRIPTION: SEQ ID NO:3:

| Asp | Tyr | Lys | Asp | Asp | Asp | Asp | Lys |
|---|---|---|---|---|---|---|---|
| 1 | | | | 5 | | | |

( 2 ) INFORMATION FOR SEQ ID NO:4:

( i ) SEQUENCE CHARACTERISTICS:
    ( A ) LENGTH: 212 amino acids
    ( B ) TYPE: amino acid
    ( C ) STRANDEDNESS: Not Relevant
    ( D ) TOPOLOGY: linear ( i i ) MOLECULE TYPE: protein (vi) ORIGINAL SOURCE:
    (A) ORGANISM: Human (vii) IMMEDIATE SOURCE:
    (B) CLONE: IgG1 Fc (xi) SEQUENCE DESCRIPTION: SEQ ID NO:4:

| Arg | Ser | Cys | Asp | Lys | Thr | His | Thr | Cys | Pro | Pro | Cys | Pro | Ala | Pro | Glu |
|---|---|---|---|---|---|---|---|---|---|---|---|---|---|---|---|
| 1 |  |  |  | 5 |  |  |  |  | 10 |  |  |  |  | 15 |  |
| Leu | Leu | Gly | Gly | Pro | Ser | Val | Phe | Leu | Phe | Pro | Pro | Lys | Pro | Lys | Asp |
|  |  |  | 20 |  |  |  |  | 25 |  |  |  |  | 30 |  |  |
| Thr | Leu | Met | Ile | Ser | Arg | Thr | Pro | Glu | Val | Thr | Cys | Val | Val | Val | Asp |
|  |  |  | 35 |  |  |  | 40 |  |  |  |  | 45 |  |  |  |
| Val | Ser | His | Glu | Asp | Pro | Glu | Val | Lys | Phe | Asn | Trp | Tyr | Val | Asp | Gly |
|  | 50 |  |  |  |  | 55 |  |  |  |  |  | 60 |  |  |  |
| Val | Glu | Val | His | Asn | Ala | Lys | Thr | Lys | Pro | Arg | Glu | Glu | Gln | Tyr | Asn |
| 65 |  |  |  |  | 70 |  |  |  |  | 75 |  |  |  |  | 80 |
| Ser | Thr | Tyr | Arg | Val | Val | Ser | Val | Leu | Thr | Val | Leu | His | Gln | Asp | Trp |
|  |  |  |  | 85 |  |  |  |  | 90 |  |  |  |  | 95 |  |
| Leu | Asn | Gly | Lys | Glu | Tyr | Lys | Cys | Lys | Val | Ser | Asn | Lys | Ala | Leu | Pro |
|  |  |  | 100 |  |  |  |  | 105 |  |  |  |  | 110 |  |  |
| Ala | Pro | Ile | Glu | Lys | Thr | Ile | Ser | Lys | Ala | Lys | Gly | Gln | Pro | Arg | Glu |
|  |  | 115 |  |  |  |  | 120 |  |  |  |  | 125 |  |  |  |
| Pro | Gln | Val | Tyr | Thr | Leu | Pro | Pro | Ser | Arg | Asp | Glu | Leu | Thr | Lys | Asn |
|  | 130 |  |  |  |  | 135 |  |  |  |  | 140 |  |  |  |  |
| Gln | Val | Ser | Leu | Thr | Cys | Leu | Val | Lys | Gly | Phe | Tyr | Pro | Ser | Asp | Ile |
| 145 |  |  |  |  | 150 |  |  |  |  | 155 |  |  |  |  | 160 |
| Ala | Val | Glu | Trp | Glu | Ser | Asn | Gly | Gln | Pro | Glu | Asn | Asn | Tyr | Lys | Thr |
|  |  |  |  | 165 |  |  |  |  | 170 |  |  |  |  | 175 |  |
| Thr | Pro | Pro | Val | Leu | Asp | Ser | Asp | Gly | Ser | Phe | Phe | Leu | Tyr | Ser | Lys |
|  |  |  | 180 |  |  |  |  | 185 |  |  |  |  | 190 |  |  |
| Leu | Thr | Val | Asp | Lys | Ser | Arg | Trp | Gln | Gln | Gly | Asn | Val | Phe | Ser | Cys |
|  |  | 195 |  |  |  |  | 200 |  |  |  |  | 205 |  |  |  |
| Ser | Val | Met | His |
|  |  | 210 |  |

(2) INFORMATION FOR SEQ ID NO:5:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: linear (ii) MOLECULE TYPE: peptide (vii) IMMEDIATE SOURCE:
        (B) CLONE: Polylinker (xi) SEQUENCE DESCRIPTION: SEQ ID NO:5:

| Gly | Gly | Gly | Gly | Ser | Gly | Gly | Gly | Gly | Ser | Gly | Gly | Gly | Gly |
|---|---|---|---|---|---|---|---|---|---|---|---|---|---|
| 1 |  |  |  | 5 |  |  |  |  | 10 |  |  |  |  |

(2) INFORMATION FOR SEQ ID NO:6:

(i) SEQUENCE CHARACTERISTICS:
        (A) LENGTH: 498 base pairs
        (B) TYPE: nucleic acid
        (C) STRANDEDNESS: single
        (D) TOPOLOGY: linear (ii) MOLECULE TYPE: cDNA to mRNA ( i i i ) HYPOTHETICAL: NO ( i v ) ANTI-SENSE: NO ( v i ) ORIGINAL SOURCE:
  ( A ) ORGANISM: Murine CTLA-8

( i x ) FEATURE:
  ( A ) NAME/KEY: CDS
  ( B ) LOCATION: 14..490

( i x ) FEATURE:
  ( A ) NAME/KEY: sig_peptide
  ( B ) LOCATION: 14..88

( i x ) FEATURE:
  ( A ) NAME/KEY: mat_peptide
  ( B ) LOCATION: 89..487

( x i ) SEQUENCE DESCRIPTION: SEQ ID NO:6:

```
GTCGACCCCC ACC ATG TTC CAT GTT TCT TTT AGA TAT ATC TTT GGA ATT           49
            Met Phe His Val Ser Phe Arg Tyr Ile Phe Gly Ile
            -25             -20                     -15

CCT CCA CTG ATC CTT GTT CTG CTG CCT GTC ACT AGT TCT GCG GTA CTC          97
Pro Pro Leu Ile Leu Val Leu Leu Pro Val Thr Ser Ser Ala Val Leu
        -10                 -5                       1

ATC CCT CAA AGT TCA GCG TGT CCA AAC ACT GAG GCC AAG GAC TTC CTC         145
Ile Pro Gln Ser Ser Ala Cys Pro Asn Thr Glu Ala Lys Asp Phe Leu
     5                   10                  15

CAG AAT GTG AAG GTC AAC CTC AAA GTC TTT AAC TCC CTT GGC GCA AAA         193
Gln Asn Val Lys Val Asn Leu Lys Val Phe Asn Ser Leu Gly Ala Lys
20                  25                  30                  35

GTG AGC TCC AGA AGG CCC TCA GAC TAC CTC AAC CGT TCC ACG TCA CCC         241
Val Ser Ser Arg Arg Pro Ser Asp Tyr Leu Asn Arg Ser Thr Ser Pro
                40                  45                  50

TGG ACT CTC CAC CGC AAT GAA GAC CCT GAT AGA TAT CCC TCT GTG ATC         289
Trp Thr Leu His Arg Asn Glu Asp Pro Asp Arg Tyr Pro Ser Val Ile
            55                  60                  65

TGG GAA GCT CAG TGC CGC CAC CAG CGC TGT GTC AAT GCG GAG GGA AAG         337
Trp Glu Ala Gln Cys Arg His Gln Arg Cys Val Asn Ala Glu Gly Lys
        70                  75                  80

CTG GAC CAC CAC ATG AAT TCT GTT CTC ATC CAG CAA GAG ATC CTG GTC         385
Leu Asp His His Met Asn Ser Val Leu Ile Gln Gln Glu Ile Leu Val
    85                  90                  95

CTG AAG AGG GAG CCT GAG AGC TGC CCC TTC ACT TTC AGG GTC GAG AAG         433
Leu Lys Arg Glu Pro Glu Ser Cys Pro Phe Thr Phe Arg Val Glu Lys
100             105                 110                 115

ATG CTG GTG GGT GTG GGC TGC ACC TGC GTG GCC TCG ATT GTC CGC CAT         481
Met Leu Val Gly Val Gly Cys Thr Cys Val Ala Ser Ile Val Arg His
            120                 125                 130

GCG TCC TAA GCGGCCGC                                                    498
Ala Ser *
```

( 2 ) INFORMATION FOR SEQ ID NO:7:

( i ) SEQUENCE CHARACTERISTICS:
    ( A ) LENGTH: 158 amino acids
    ( B ) TYPE: amino acid
    ( D ) TOPOLOGY: linear ( i i ) MOLECULE TYPE: protein ( x i ) SEQUENCE DESCRIPTION: SEQ ID NO:7:

```
Met Phe His Val Ser Phe Arg Tyr Ile Phe Gly Ile Pro Pro Leu Ile
-25             -20                 -15                 -10
```

```
Leu  Val  Leu  Leu  Pro  Val  Thr  Ser  Ser  Ala  Val  Leu  Ile  Pro  Gln  Ser
              -5                        1                    5

Ser  Ala  Cys  Pro  Asn  Thr  Glu  Ala  Lys  Asp  Phe  Leu  Gln  Asn  Val  Lys
          10                       15                      20

Val  Asn  Leu  Lys  Val  Phe  Asn  Ser  Leu  Gly  Ala  Lys  Val  Ser  Ser  Arg
      25                       30                    35

Arg  Pro  Ser  Asp  Tyr  Leu  Asn  Arg  Ser  Thr  Ser  Pro  Trp  Thr  Leu  His
 40                       45                      50                           55

Arg  Asn  Glu  Asp  Pro  Asp  Arg  Tyr  Pro  Ser  Val  Ile  Trp  Glu  Ala  Gln
                 60                       65                            70

Cys  Arg  His  Gln  Arg  Cys  Val  Asn  Ala  Glu  Gly  Lys  Leu  Asp  His  His
               75                       80                         85

Met  Asn  Ser  Val  Leu  Ile  Gln  Gln  Glu  Ile  Leu  Val  Leu  Lys  Arg  Glu
           90                       95                     100

Pro  Glu  Ser  Cys  Pro  Phe  Thr  Phe  Arg  Val  Glu  Lys  Met  Leu  Val  Gly
          105                      110                     115

Val  Gly  Cys  Thr  Cys  Val  Ala  Ser  Ile  Val  Arg  His  Ala  Ser
120                      125                     130
```

( 2 ) INFORMATION FOR SEQ ID NO:8:

( i ) SEQUENCE CHARACTERISTICS:
        ( A ) LENGTH: 151 amino acids
        ( B ) TYPE: amino acid
        ( C ) STRANDEDNESS: Not Relevant
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Herpesvirus Saimiri
        ( B ) STRAIN: ORF13

( x i ) SEQUENCE DESCRIPTION: SEQ ID NO:8:

```
Met  Thr  Phe  Arg  Met  Thr  Ser  Leu  Val  Leu  Leu  Leu  Leu  Ser  Ile
 1                    5                       10                          15

Asp  Cys  Ile  Val  Lys  Ser  Glu  Ile  Thr  Ser  Ala  Gln  Thr  Pro  Arg  Cys
                20                       25                      30

Leu  Ala  Ala  Asn  Asn  Ser  Phe  Pro  Arg  Ser  Val  Met  Val  Thr  Leu  Ser
           35                       40                      45

Ile  Arg  Asn  Trp  Asn  Thr  Ser  Ser  Lys  Arg  Ala  Ser  Asp  Tyr  Tyr  Asn
      50                       55                      60

Arg  Ser  Thr  Ser  Pro  Trp  Thr  Leu  His  Arg  Asn  Glu  Asp  Gln  Asp  Arg
 65                       70                      75                           80

Tyr  Pro  Ser  Val  Ile  Trp  Glu  Ala  Lys  Cys  Arg  Tyr  Leu  Gly  Cys  Val
                     85                       90                           95

Asn  Ala  Asp  Gly  Asn  Val  Asp  Tyr  His  Met  Asn  Ser  Val  Pro  Ile  Gln
               100                      105                     110

Gln  Glu  Ile  Leu  Val  Val  Arg  Lys  Gly  His  Gln  Pro  Cys  Pro  Asn  Ser
           115                      120                     125

Phe  Arg  Leu  Glu  Lys  Met  Leu  Val  Thr  Val  Gly  Cys  Thr  Cys  Val  Thr
      130                      135                     140

Pro  Ile  Val  His  Asn  Val  Asp
145                      150
```

( 2 ) INFORMATION FOR SEQ ID NO:9:

( i ) SEQUENCE CHARACTERISTICS:
    ( A ) LENGTH: 3223 base pairs
    ( B ) TYPE: nucleic acid
    ( C ) STRANDEDNESS: single
    ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
    ( A ) ORGANISM: Human
    ( B ) STRAIN: IL-17 R (hCTLA8 receptor)

( i x ) FEATURE:
    ( A ) NAME/KEY: CDS
    ( B ) LOCATION: 93..2693

( x i ) SEQUENCE DESCRIPTION: SEQ ID NO:9:

```
GGGAGACCGG  AATTCCGGGA  AAAGAAAGCC  TCAGAACGTT  CGCTCGCTGC  GTCCCCAGCC          60

GGGGCCGAGC  CCTCCGCGAC  GCCACCCGGG  CC ATG GGG GCC GCA CGC AGC CCG             113
                                      Met Gly Ala Ala Arg Ser Pro
                                       1               5

CCG TCC GCT GTC CCG GGG CCC CTG CTG GGG CTG CTC CTG CTG CTC CTG               161
Pro Ser Ala Val Pro Gly Pro Leu Leu Gly Leu Leu Leu Leu Leu Leu
         10              15                  20

GGC GTG CTG GCC CCG GGT GGC GCC TCC CTG CGA CTC CTG GAC CAC CGG               209
Gly Val Leu Ala Pro Gly Gly Ala Ser Leu Arg Leu Leu Asp His Arg
         25              30                  35

GCG CTG GTC TGC TCC CAG CCG GGG CTA AAC TGC ACG GTC AAG AAT AGT               257
Ala Leu Val Cys Ser Gln Pro Gly Leu Asn Cys Thr Val Lys Asn Ser
 40              45                  50                  55

ACC TGC CTG GAT GAC AGC TGG ATT CAC CCT CGA AAC CTG ACC CCC TCC               305
Thr Cys Leu Asp Asp Ser Trp Ile His Pro Arg Asn Leu Thr Pro Ser
                 60                  65                  70

TCC CCA AAG GAC CTG CAG ATC CAG CTG CAC TTT GCC CAC ACC CAA CAA               353
Ser Pro Lys Asp Leu Gln Ile Gln Leu His Phe Ala His Thr Gln Gln
             75                  80                  85

GGA GAC CTG TTC CCC GTG GCT CAC ATC GAA TGG ACA CTG CAG ACA GAC               401
Gly Asp Leu Phe Pro Val Ala His Ile Glu Trp Thr Leu Gln Thr Asp
         90                  95                 100

GCC AGC ATC CTG TAC CTC GAG GGT GCA GAG TTA TCT GTC CTG CAG CTG               449
Ala Ser Ile Leu Tyr Leu Glu Gly Ala Glu Leu Ser Val Leu Gln Leu
 105                 110                 115

AAC ACC AAT GAA CGT TTG TGC GTC AGG TTT GAG TTT CTG TCC AAA CTG               497
Asn Thr Asn Glu Arg Leu Cys Val Arg Phe Glu Phe Leu Ser Lys Leu
 120                 125                 130                 135

AGG CAT CAC CAC AGG CGG TGG CGT TTT ACC TTC AGC CAC TTT GTG GTT               545
Arg His His His Arg Arg Trp Arg Phe Thr Phe Ser His Phe Val Val
                 140                 145                 150

GAC CCT GAC CAG GAA TAT GAG GTG ACC GTT CAC CAC CTG CCC AAG CCC               593
Asp Pro Asp Gln Glu Tyr Glu Val Thr Val His His Leu Pro Lys Pro
             155                 160                 165

ATC CCT GAT GGG GAC CCA AAC CAC CAG TCC AAG AAT TTC CTT GTG CCT               641
Ile Pro Asp Gly Asp Pro Asn His Gln Ser Lys Asn Phe Leu Val Pro
         170                 175                 180

GAC TGT GAG CAC GCC AGG ATG AAG GTA ACC ACG CCA TGC ATG AGC TCA               689
Asp Cys Glu His Ala Arg Met Lys Val Thr Thr Pro Cys Met Ser Ser
 185                 190                 195

GGC AGC CTG TGG GAC CCC AAC ATC ACC GTG GAG ACC CTG GAG GCC CAC               737
Gly Ser Leu Trp Asp Pro Asn Ile Thr Val Glu Thr Leu Glu Ala His
 200                 205                 210                 215
```

```
CAG CTG CGT GTG AGC TTC ACC CTG TGG AAC GAA TCT ACC CAT TAC CAG     785
Gln Leu Arg Val Ser Phe Thr Leu Trp Asn Glu Ser Thr His Tyr Gln
            220                 225                 230

ATC CTG CTG ACC AGT TTT CCG CAC ATG GAG AAC CAC AGT TGC TTT GAG     833
Ile Leu Leu Thr Ser Phe Pro His Met Glu Asn His Ser Cys Phe Glu
                235                 240                 245

CAC ATG CAC CAC ATA CCT GCG CCC AGA CCA GAA GAG TTC CAC CAG CGA     881
His Met His His Ile Pro Ala Pro Arg Pro Glu Glu Phe His Gln Arg
        250                 255                 260

TCC AAC GTC ACA CTC ACT CTA CGC AAC CTT AAA GGG TGC TGT CGC CAC     929
Ser Asn Val Thr Leu Thr Leu Arg Asn Leu Lys Gly Cys Cys Arg His
    265                 270                 275

CAA GTG CAG ATC CAG CCC TTC TTC AGC AGC TGC CTC AAT GAC TGC CTC     977
Gln Val Gln Ile Gln Pro Phe Phe Ser Ser Cys Leu Asn Asp Cys Leu
280                 285                 290                 295

AGA CAC TCC GCG ACT GTT TCC TGC CCA GAA ATG CCA GAC ACT CCA GAA    1025
Arg His Ser Ala Thr Val Ser Cys Pro Glu Met Pro Asp Thr Pro Glu
                300                 305                 310

CCA ATT CCG GAC TAC ATG CCC CTG TGG GTG TAC TGG TTC ATC ACG GGC    1073
Pro Ile Pro Asp Tyr Met Pro Leu Trp Val Tyr Trp Phe Ile Thr Gly
            315                 320                 325

ATC TCC ATC CTG CTG GTG GGC TCC GTC ATC CTG CTC ATC GTC TGC ATG    1121
Ile Ser Ile Leu Leu Val Gly Ser Val Ile Leu Leu Ile Val Cys Met
                330                 335                 340

ACC TGG AGG CTA GCT GGG CCT GGA AGT GAA AAA TAC AGT GAT GAC ACC    1169
Thr Trp Arg Leu Ala Gly Pro Gly Ser Glu Lys Tyr Ser Asp Asp Thr
        345                 350                 355

AAA TAC ACC GAT GGC CTG CCT GCG GCT GAC CTG ATC CCC CCA CCG CTG    1217
Lys Tyr Thr Asp Gly Leu Pro Ala Ala Asp Leu Ile Pro Pro Pro Leu
360                 365                 370                 375

AAG CCC AGG AAG GTC TGG ATC ATC TAC TCA GCC GAC CAC CCC CTC TAC    1265
Lys Pro Arg Lys Val Trp Ile Ile Tyr Ser Ala Asp His Pro Leu Tyr
            380                 385                 390

GTG GAC GTG GTC CTG AAA TTC GCC CAG TTC CTG CTC ACC GCC TGC GGC    1313
Val Asp Val Val Leu Lys Phe Ala Gln Phe Leu Leu Thr Ala Cys Gly
                395                 400                 405

ACG GAA GTG GCC CTG GAC CTG CTG GAA GAG CAG GCC ATC TCG GAG GCA    1361
Thr Glu Val Ala Leu Asp Leu Leu Glu Glu Gln Ala Ile Ser Glu Ala
        410                 415                 420

GGA GTC ATG ACC TGG GTG GGC CGT CAG AAG CAG GAG ATG GTG GAG AGC    1409
Gly Val Met Thr Trp Val Gly Arg Gln Lys Gln Glu Met Val Glu Ser
425                 430                 435

AAC TCT AAG ATC ATC GTC CTG TGC TCC CGC GGC ACG CGC GCC AAG TGG    1457
Asn Ser Lys Ile Ile Val Leu Cys Ser Arg Gly Thr Arg Ala Lys Trp
440                 445                 450                 455

CAG GCG CTC CTG GGC CGG GGG GCG CCT GTG CGG CTG CGC TGC GAC CAC    1505
Gln Ala Leu Leu Gly Arg Gly Ala Pro Val Arg Leu Arg Cys Asp His
            460                 465                 470

GGA AAG CCC GTG GGG GAC CTG TTC ACT GCA GCC ATG AAC ATG ATC CTC    1553
Gly Lys Pro Val Gly Asp Leu Phe Thr Ala Ala Met Asn Met Ile Leu
        475                 480                 485

CCG GAC TTC AAG AGG CCA GCC TGC TTC GGC ACC TAC GTA GTC TGC TAC    1601
Pro Asp Phe Lys Arg Pro Ala Cys Phe Gly Thr Tyr Val Val Cys Tyr
        490                 495                 500

TTC AGC GAG GTC AGC TGT GAC GGC GAC GTC CCC GAC CTG TTC GGC GCG    1649
Phe Ser Glu Val Ser Cys Asp Gly Asp Val Pro Asp Leu Phe Gly Ala
    505                 510                 515

GCG CCG CGG TAC CCG CTC ATG GAC AGG TTC GAG GAG GTG TAC TTC CGC    1697
Ala Pro Arg Tyr Pro Leu Met Asp Arg Phe Glu Glu Val Tyr Phe Arg
520                 525                 530                 535
```

```
ATC CAG GAC CTG GAG ATG TTC CAG CCG GGC CGC ATG CAC CGC GTA GGG      1745
Ile Gln Asp Leu Glu Met Phe Gln Pro Gly Arg Met His Arg Val Gly
            540                 545                 550

GAG CTG TCG GGG GAC AAC TAC CTG CGG AGC CCG GGC GGC AGG CAG CTC      1793
Glu Leu Ser Gly Asp Asn Tyr Leu Arg Ser Pro Gly Gly Arg Gln Leu
        555                 560                 565

CGC GCC GCC CTG GAC AGG TTC CGG GAC TGG CAG GTC CGC TGT CCC GAC      1841
Arg Ala Ala Leu Asp Arg Phe Arg Asp Trp Gln Val Arg Cys Pro Asp
        570                 575                 580

TGG TTC GAA TGT GAG AAC CTC TAC TCA GCA GAT GAC CAG GAT GCC CCG      1889
Trp Phe Glu Cys Glu Asn Leu Tyr Ser Ala Asp Asp Gln Asp Ala Pro
585                 590                 595

TCC CTG GAC GAA GAG GTG TTT GAG GAG CCA CTG CTG CCT CCG GGA ACC      1937
Ser Leu Asp Glu Glu Val Phe Glu Glu Pro Leu Leu Pro Pro Gly Thr
600                 605                 610                 615

GGC ATC GTG AAG CGG GCG CCC CTG GTG CGC GAG CCT GGC TCC CAG GCC      1985
Gly Ile Val Lys Arg Ala Pro Leu Val Arg Glu Pro Gly Ser Gln Ala
            620                 625                 630

TGC CTG GCC ATA GAC CCG CTG GTC GGG GAG GAA GGA GGA GCA GCA GTG      2033
Cys Leu Ala Ile Asp Pro Leu Val Gly Glu Glu Gly Gly Ala Ala Val
                635                 640                 645

GCA AAG CTG GAA CCT CAC CTG CAG CCC CGG GGT CAG CCA GCG CCG CAG      2081
Ala Lys Leu Glu Pro His Leu Gln Pro Arg Gly Gln Pro Ala Pro Gln
        650                 655                 660

CCC CTC CAC ACC CTG GTG CTC GCC GCA GAG GAG GGG GCC CTG GTG GCC      2129
Pro Leu His Thr Leu Val Leu Ala Ala Glu Glu Gly Ala Leu Val Ala
    665                 670                 675

GCG GTG GAG CCT GGG CCC CTG GCT GAC GGT GCC GCA GTC CGG CTG GCA      2177
Ala Val Glu Pro Gly Pro Leu Ala Asp Gly Ala Ala Val Arg Leu Ala
680                 685                 690                 695

CTG GCG GGG GAG GGC GAG GCC TGC CCG CTG CTG GGC AGC CCG GGC GCT      2225
Leu Ala Gly Glu Gly Glu Ala Cys Pro Leu Leu Gly Ser Pro Gly Ala
                700                 705                 710

GGG CGA AAT AGC GTC CTC TTC CTC CCC GTG GAC CCC GAG GAC TCG CCC      2273
Gly Arg Asn Ser Val Leu Phe Leu Pro Val Asp Pro Glu Asp Ser Pro
            715                 720                 725

CTT GGC AGC AGC ACC CCC ATG GCG TCT CCT GAC CTC CTT CCA GAG GAC      2321
Leu Gly Ser Ser Thr Pro Met Ala Ser Pro Asp Leu Leu Pro Glu Asp
        730                 735                 740

GTG AGG GAG CAC CTC GAA GGC TTG ATG CTC TCG CTC TTC GAG CAG AGT      2369
Val Arg Glu His Leu Glu Gly Leu Met Leu Ser Leu Phe Glu Gln Ser
    745                 750                 755

CTG AGC TGC CAG GCC CAG GGG GGC TGC AGT AGA CCC GCC ATG GTC CTC      2417
Leu Ser Cys Gln Ala Gln Gly Gly Cys Ser Arg Pro Ala Met Val Leu
760                 765                 770                 775

ACA GAC CCA CAC ACG CCC TAC GAG GAG GAG CAG CGG CAG TCA GTG CAG      2465
Thr Asp Pro His Thr Pro Tyr Glu Glu Glu Gln Arg Gln Ser Val Gln
                780                 785                 790

TCT GAC CAG GGC TAC ATC TCC AGG AGC TCC CCG CAG CCC CCC GAG GGA      2513
Ser Asp Gln Gly Tyr Ile Ser Arg Ser Ser Pro Gln Pro Pro Glu Gly
            795                 800                 805

CTC ACG GAA ATG GAG GAA GAG GAA GAG GAG CAG GAC CCA GGG AAG          2561
Leu Thr Glu Met Glu Glu Glu Glu Glu Glu Gln Asp Pro Gly Lys
        810                 815                 820

CCG GCC CTG CCA CTC TCT CCC GAG GAC CTG GAG AGC CTG AGG AGC CTC      2609
Pro Ala Leu Pro Leu Ser Pro Glu Asp Leu Glu Ser Leu Arg Ser Leu
825                 830                 835

CAG CGG CAG CTG CTT TTC CGC CAG CTG CAG AAG AAC TCG GGC TGG GAC      2657
Gln Arg Gln Leu Leu Phe Arg Gln Leu Gln Lys Asn Ser Gly Trp Asp
840                 845                 850                 855
```

```
ACG ATG GGG TCA GAG TCA GAG GGG CCC AGT GCA TGA GGGCGGCTCC         2703
Thr Met Gly Ser Glu Ser Glu Gly Pro Ser Ala *
                860                 865

CCAGGGACCG  CCCAGATCCC  AGCTTTGAGA  GAGGAGTGTG  TGTGCACGTA  TTCATCTGTG   2763

TGTACATGTC  TGCATGTGTA  TATGTTCGTG  TGTGAAATGT  AGGCTTTAAA  ATGTAAATGT   2823

CTGGATTTTA  ATCCCAGGCA  TCCCTCCTAA  CTTTTCTTTG  TGCAGCGGTC  TGGTTATCGT   2883

CTATCCCCAG  GGGAATCCAC  ACAGCCCGCT  CCCAGGAGCT  AATGGTAGAG  CGTCCTTGAG   2943

GCTCCATTAT  TCGTTCATTC  AGCATTTATT  GTGCACCTAC  TATGTGGCGG  GCATTTGGGA   3003

TACCAAGATA  AATTGCATGC  GGCATGGCCC  CAGCCATGAA  GGAACTTAAC  CGCTAGTGCC   3063

GAGGACACGT  TAAACGAACA  GGATGGGCCG  GGCACGGTGG  CTCACGCCTG  TAATCCCAGC   3123

ACACTGGGAG  GCCGAGGCAG  GTGGATCACT  CTGAGGTCAG  GAGTTTGAGC  CAGCCTGGCC   3183

AACATGGTGA  AACCCCGGAA  TTCGAGCTCG  GTACCCGGGG                           3223
```

( 2 ) INFORMATION FOR SEQ ID NO:10:

( i ) SEQUENCE CHARACTERISTICS:
        ( A ) LENGTH: 866 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Gly Ala Ala Arg Ser Pro Pro Ser Ala Val Pro Gly Pro Leu Leu
 1               5                  10                  15

Gly Leu Leu Leu Leu Leu Leu Gly Val Leu Ala Pro Gly Gly Ala Ser
                20                  25                  30

Leu Arg Leu Leu Asp His Arg Ala Leu Val Cys Ser Gln Pro Gly Leu
            35                  40                  45

Asn Cys Thr Val Lys Asn Ser Thr Cys Leu Asp Asp Ser Trp Ile His
        50                  55                  60

Pro Arg Asn Leu Thr Pro Ser Pro Lys Asp Leu Gln Ile Gln Leu
 65                  70                  75                  80

His Phe Ala His Thr Gln Gln Gly Asp Leu Phe Pro Val Ala His Ile
                    85                  90                  95

Glu Trp Thr Leu Gln Thr Asp Ala Ser Ile Leu Tyr Leu Glu Gly Ala
                100                 105                 110

Glu Leu Ser Val Leu Gln Leu Asn Thr Asn Glu Arg Leu Cys Val Arg
            115                 120                 125

Phe Glu Phe Leu Ser Lys Leu Arg His His Arg Arg Trp Arg Phe
        130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                    165                 170                 175

Ser Lys Asn Phe Leu Val Pro Asp Cys Glu His Ala Arg Met Lys Val
                180                 185                 190

Thr Thr Pro Cys Met Ser Ser Gly Ser Leu Trp Asp Pro Asn Ile Thr
            195                 200                 205

Val Glu Thr Leu Glu Ala His Gln Leu Arg Val Ser Phe Thr Leu Trp
        210                 215                 220

Asn Glu Ser Thr His Tyr Gln Ile Leu Leu Thr Ser Phe Pro His Met
225                 230                 235                 240
```

```
Glu  Asn  His  Ser  Cys  Phe  Glu  His  Met  His  His  Ile  Pro  Ala  Pro  Arg
               245                      250                      255

Pro  Glu  Glu  Phe  His  Gln  Arg  Ser  Asn  Val  Thr  Leu  Thr  Leu  Arg  Asn
               260                      265                      270

Leu  Lys  Gly  Cys  Cys  Arg  His  Gln  Val  Gln  Ile  Gln  Pro  Phe  Phe  Ser
          275                      280                      285

Ser  Cys  Leu  Asn  Asp  Cys  Leu  Arg  His  Ser  Ala  Thr  Val  Ser  Cys  Pro
     290                      295                      300

Glu  Met  Pro  Asp  Thr  Pro  Glu  Pro  Ile  Pro  Asp  Tyr  Met  Pro  Leu  Trp
305                      310                      315                      320

Val  Tyr  Trp  Phe  Ile  Thr  Gly  Ile  Ser  Ile  Leu  Leu  Val  Gly  Ser  Val
                    325                      330                      335

Ile  Leu  Leu  Ile  Val  Cys  Met  Thr  Trp  Arg  Leu  Ala  Gly  Pro  Gly  Ser
               340                      345                      350

Glu  Lys  Tyr  Ser  Asp  Asp  Thr  Lys  Tyr  Thr  Asp  Gly  Leu  Pro  Ala  Ala
          355                      360                      365

Asp  Leu  Ile  Pro  Pro  Pro  Leu  Lys  Pro  Arg  Lys  Val  Trp  Ile  Ile  Tyr
     370                      375                      380

Ser  Ala  Asp  His  Pro  Leu  Tyr  Val  Asp  Val  Val  Leu  Lys  Phe  Ala  Gln
385                      390                      395                      400

Phe  Leu  Leu  Thr  Ala  Cys  Gly  Thr  Glu  Val  Ala  Leu  Asp  Leu  Leu  Glu
               405                      410                      415

Glu  Gln  Ala  Ile  Ser  Glu  Ala  Gly  Val  Met  Thr  Trp  Val  Gly  Arg  Gln
               420                      425                      430

Lys  Gln  Glu  Met  Val  Glu  Ser  Asn  Ser  Lys  Ile  Ile  Val  Leu  Cys  Ser
          435                      440                      445

Arg  Gly  Thr  Arg  Ala  Lys  Trp  Gln  Ala  Leu  Leu  Gly  Arg  Gly  Ala  Pro
     450                      455                      460

Val  Arg  Leu  Arg  Cys  Asp  His  Gly  Lys  Pro  Val  Gly  Asp  Leu  Phe  Thr
465                      470                      475                      480

Ala  Ala  Met  Asn  Met  Ile  Leu  Pro  Asp  Phe  Lys  Arg  Pro  Ala  Cys  Phe
                    485                      490                      495

Gly  Thr  Tyr  Val  Val  Cys  Tyr  Phe  Ser  Glu  Val  Ser  Cys  Asp  Gly  Asp
               500                      505                      510

Val  Pro  Asp  Leu  Phe  Gly  Ala  Ala  Pro  Arg  Tyr  Pro  Leu  Met  Asp  Arg
          515                      520                      525

Phe  Glu  Glu  Val  Tyr  Phe  Arg  Ile  Gln  Asp  Leu  Glu  Met  Phe  Gln  Pro
530                      535                      540

Gly  Arg  Met  His  Arg  Val  Gly  Glu  Leu  Ser  Gly  Asp  Asn  Tyr  Leu  Arg
545                      550                      555                      560

Ser  Pro  Gly  Gly  Arg  Gln  Leu  Arg  Ala  Ala  Leu  Asp  Arg  Phe  Arg  Asp
               565                      570                      575

Trp  Gln  Val  Arg  Cys  Pro  Asp  Trp  Phe  Glu  Cys  Glu  Asn  Leu  Tyr  Ser
               580                      585                      590

Ala  Asp  Asp  Gln  Asp  Ala  Pro  Ser  Leu  Asp  Glu  Glu  Val  Phe  Glu  Glu
          595                      600                      605

Pro  Leu  Leu  Pro  Pro  Gly  Thr  Gly  Ile  Val  Lys  Arg  Ala  Pro  Leu  Val
     610                      615                      620

Arg  Glu  Pro  Gly  Ser  Gln  Ala  Cys  Leu  Ala  Ile  Asp  Pro  Leu  Val  Gly
625                      630                      635                      640

Glu  Glu  Gly  Gly  Ala  Ala  Val  Ala  Lys  Leu  Glu  Pro  His  Leu  Gln  Pro
               645                      650                      655

Arg  Gly  Gln  Pro  Ala  Pro  Gln  Pro  Leu  His  Thr  Leu  Val  Leu  Ala  Ala
               660                      665                      670
```

| | | | | | | | | | | | | | | |
|---|---|---|---|---|---|---|---|---|---|---|---|---|---|---|
| Glu | Glu | Gly 675 | Ala | Leu | Val | Ala | Ala 680 | Val | Glu | Pro | Gly 685 | Leu | Ala | Asp |
| Gly | Ala 690 | Ala | Val | Arg | Leu | Ala 695 | Leu | Ala | Gly | Glu 700 | Glu | Ala | Cys | Pro |
| Leu 705 | Leu | Gly | Ser | Pro | Gly 710 | Ala | Gly | Arg | Asn | Ser 715 | Val | Leu | Phe | Leu | Pro 720 |
| Val | Asp | Pro | Glu | Asp 725 | Ser | Pro | Leu | Gly | Ser 730 | Ser | Thr | Pro | Met | Ala 735 | Ser |
| Pro | Asp | Leu | Leu 740 | Pro | Glu | Asp | Val | Arg 745 | Glu | His | Leu | Glu | Gly 750 | Leu | Met |
| Leu | Ser | Leu 755 | Phe | Glu | Gln | Ser | Leu 760 | Ser | Cys | Gln | Ala | Gln 765 | Gly | Gly | Cys |
| Ser | Arg 770 | Pro | Ala | Met | Val | Leu 775 | Thr | Asp | Pro | His | Thr 780 | Pro | Tyr | Glu | Glu |
| Glu 785 | Gln | Arg | Gln | Ser | Val 790 | Gln | Ser | Asp | Gln | Gly 795 | Tyr | Ile | Ser | Arg | Ser 800 |
| Ser | Pro | Gln | Pro | Pro 805 | Glu | Gly | Leu | Thr | Glu 810 | Met | Glu | Glu | Glu 815 | Glu |
| Glu | Glu | Gln | Asp 820 | Pro | Gly | Lys | Pro | Ala 825 | Leu | Pro | Leu | Ser | Pro 830 | Glu | Asp |
| Leu | Glu | Ser 835 | Leu | Arg | Ser | Leu | Gln 840 | Arg | Gln | Leu | Leu | Phe 845 | Arg | Gln | Leu |
| Gln | Lys 850 | Asn | Ser | Gly | Trp | Asp 855 | Thr | Met | Gly | Ser | Glu 860 | Ser | Glu | Gly | Pro |
| Ser | Ala 865 |